United States Patent
Piron et al.

(10) Patent No.: US 10,448,858 B2
(45) Date of Patent: Oct. 22, 2019

(54) INDWELLING RADIO FREQUENCY COILS FOR INTRAOPERATIVE MAGNETIC RESONANCE IMAGING

(71) Applicant: SYNAPTIVE MEDICAL (BARBADOS) INC., Bridgetown (BB)

(72) Inventors: Cameron Anthony Piron, Toronto (CA); Thanh Vinh Vuong, Toronto (CA); Murugathas Yuwaraj, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 31 days.

(21) Appl. No.: 15/490,258

(22) Filed: Apr. 18, 2017

(65) Prior Publication Data
US 2018/0299520 A1    Oct. 18, 2018

(51) Int. Cl.
| | | |
|---|---|---|
| G01V 3/00 | (2006.01) | |
| A61B 5/055 | (2006.01) | |
| G01R 33/34 | (2006.01) | |
| G01R 33/3415 | (2006.01) | |
| G01R 33/345 | (2006.01) | |
| G01R 33/561 | (2006.01) | |
| A61B 5/00 | (2006.01) | |

(52) U.S. Cl.
CPC ........ *A61B 5/055* (2013.01); *G01R 33/34007* (2013.01); *A61B 5/0037* (2013.01); *A61B 2505/05* (2013.01); *G01R 33/3415* (2013.01); *G01R 33/3456* (2013.01); *G01R 33/5611* (2013.01)

(58) Field of Classification Search
CPC .............................. G01R 33/34084
USPC ................................. 324/322, 318
See application file for complete search history.

(56) References Cited

U.S. PATENT DOCUMENTS

| 5,396,905 | A | * | 3/1995 | Newman | .......... | G01R 33/34084 128/853 |
| 5,414,358 | A | * | 5/1995 | Eilenberg | ................ | G01R 33/28 324/309 |
| 5,865,177 | A | * | 2/1999 | Segawa | ................. | A61B 5/0555 324/318 |
| 2006/0279284 | A1 | * | 12/2006 | Vaughan | ............. | G01R 33/3692 324/318 |

(Continued)

FOREIGN PATENT DOCUMENTS

WO    2014138923    9/2014

OTHER PUBLICATIONS

RAPID Biomedical, miniflex coils * MR Coils Made to Measure, Version Aug. 2017, copyright: RAPID Biomedical GmbH, 1 p. Accessed online at: https://www.rapidbiomed.de/wp-content/uploads/2013/06/miniflex-coil-2017-08-29.pdf.

*Primary Examiner* — Louis M Arana
(74) *Attorney, Agent, or Firm* — Quarles & Brady LLP; Jonathan D. Stone

(57) ABSTRACT

Radio frequency ("RF") coil assemblies for use in local magnetic resonance imaging ("MRI") of tissues in a subject or patient in an intraoperative setting are provided. One or more RF coils are coupled to an absorbent member. A connecting element is coupled to the RF coil(s) or the absorbent member. When connected to the RF coil(s), the connecting element includes a wired connector that communicates signals between the RF coil(s) and an RF controller. The RF coil assemblies can be made to be disposable.

16 Claims, 16 Drawing Sheets

(56) References Cited

U.S. PATENT DOCUMENTS

2010/0256481 A1     10/2010   Mareci
2012/0223705 A1      9/2012   Lowery
2016/0022146 A1      1/2016   Piron
2016/0363641 A1*   12/2016   Finnerty ............ G01R 33/3415

* cited by examiner

INDWELLING RADIO FREQUENCY COILS FOR INTRAOPERATIVE MAGNETIC RESONANCE IMAGING

BACKGROUND

The present disclosure relates to radio frequency coils for use in an intraoperative setting.

SUMMARY OF THE DISCLOSURE

It is an aspect of the present disclosure to provide a radio frequency ("RF") coil assembly for use in an intraoperative setting. The RF coil assembly includes an absorbent member comprising an absorbent material, an RF coil coupled to the absorbent member, and a connecting element. The connecting element comprises a wired connector operatively engaged with the RF coil. The wired connector communicates signals between the RF coil and an RF controller, and maintains a visual indication of a location of the absorbent member relative to tissues adjacent the absorbent member.

It is another aspect of the present disclosure to provide an RF coil assembly for use in an intraoperative setting. The RF coil assembly includes an absorbent member comprising an absorbent material, an RF coil coupled to the absorbent member, a wireless communications circuit coupled to the absorbent member and in communication with the RF coil, and a connecting element comprising a string coupled to the absorbent member. The wireless communications circuit is configured to send signals received by the RF coil to an RF receiver. The connecting member maintains a visual indication of a location of the absorbent member relative to tissues adjacent the absorbent member.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are radio frequency ("RF") coil assemblies for use in local magnetic resonance imaging ("MRI") of tissues in a subject or patient in an intraoperative setting.

As used herein, the phrase "intraoperative" refers to an action, process, method, event, or step that occurs or is carried out during at least a portion of a medical procedure. Intraoperative, as used herein, is not limited to surgical procedures, and may refer to other types of medical procedures, such as diagnostic and therapeutic procedures.

Some embodiments described in the present disclosure provide an RF coil assembly that can be used as an alternative to surface coils or volume coils for local magnetic resonance imaging of tissues in a subject or patient during an intraoperative procedure. The RF coil assembly can be provided to a cavity or exposed tissue surface to provide imaging of the tissues surrounding the RF coil assembly. In some configurations, the RF coil assembly can provide imaging of tissues at a depth beyond the tissue-facing surface of the RF coil assembly, given its close proximity to the tissues. The ability of an RF coil to detect magnetic resonance signals increases the closer the RF coil is to the tissue being imaged. RF coils that are local to the tissue-of-interest have a higher signal-to-noise ratio ("SNR") than those positioned farther away, and thereby can provide higher quality images.

Such images may be used during intraoperative procedures, potentially providing detail that would otherwise not be obtainable with current technologies, or that would only be obtainable with less resolution or SNR using currently available technologies. As one non-limiting example, the RF coil assemblies described in the present disclosure can be used to provide accurate, high-resolution imaging of a local tissue region for tumor margin delineation.

Figure 1:
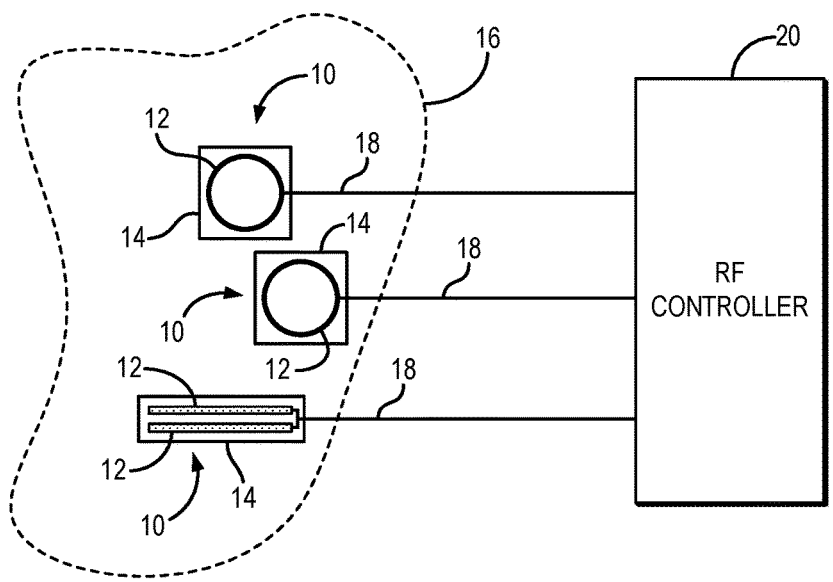
FIG. 1 illustrates example radio frequency ("RF") coil assemblies for use in intraoperative magnetic resonance imaging ("MRI") of local tissue regions.

An example of an RF coil assembly 10 for use in an intraoperative setting is shown in FIG. 1. The RF coil assembly 10 includes an RF coil 12 that is coupled to an absorbent member 14. The absorbent member 14 may be a pad, flexible sheet, sponge, or other form of absorbent material, and which is used by a surgeon to absorb or retain fluids, such as blood or other bodily fluids, during an intraoperative procedure. The absorbent member 14 can be composed of rayon, cotton, or other suitable absorbent materials. As a non-limiting list of examples, the absorbent member 14 can include a gauze sheet, a gauze pad, a surgical dressing, a hemostatic dressing, a surgical sponge, or a cotton ball, among others. The absorbent member 14 can be pre-soaked in saline, an antibiotic solution, an anti-coagulant, or other medicament. Preferably, the RF coil assemblies described in the present disclosure may be disposable.

As shown in FIG. 1, one or more RF coil assemblies 10 can be used during an intraoperative procedure. In addition, the RF coil assemblies 10 can implement different coil configurations for the RF coil 12, as illustrated in FIG. 1 and described in more detail below.

During use, the absorbent member 14 absorbs fluids, such as blood or other bodily fluids, which can make the absorbent member 14 difficult to differentiate from surrounding tissues 16; thus, the absorbent member 14 has coupled thereto a connecting element 18 that provides for easy identification and removal of the absorbent member 14 during or after an intraoperative procedure. For instance, the connecting element 18 can provide a visual indication of the one or more RF coil assemblies 10 used during an intraoperative procedure, and can also provide for removal of an RF coil assembly 10 through manipulation of the connecting element 18, such as by pulling on the connecting element 18 to withdraw the RF coil assembly 10 from being in contact with the subject or patient.

The RF coil 12 can be coupled to a surface of the absorbent member 14, or can be integrated or otherwise embedded within the absorbent member 14. For example, the RF coil 12 can be woven into the absorbent member 14, or can be disposed between two layers of absorbent materials that form the absorbent member 14. Examples of different RF coil configurations that can be implemented in the RF coil assemblies described in the present disclosure are described below. Additional examples are also described in co-pending U.S. Patent Application No. 2016/0022146, which is herein incorporated by reference in its entirety, and which is based on PCT Application Publication No. WO/2014/138923.

Figure 2A:
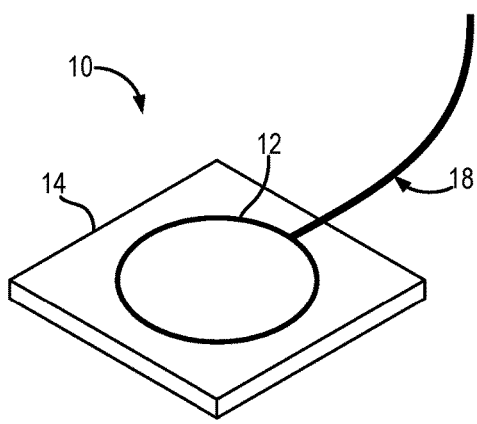
FIG. 2A shows one example of an RF coil assembly that implements a wired RF coil, wherein a wired connector communicatively couples the RF coil to an RF controller.

In one example shown in FIG. 2A, the connecting element 18 is a wired connector that operatively engages the RF coil 12 to communicate signals between the RF coil 12 and an RF controller 20. The RF controller 20 can include circuits and electronics for an RF receiver, an RF transmitter, or both. The RF receiver may be a multichannel receiver, and the RF transmitter may be a multichannel transmitter. These multichannel configurations provide for operating multiple RF coil assemblies 10 during a single intraoperative procedure. For instance, multiple RF coil assemblies 10 can be provided to implement parallel imaging, parallel transmission, or both.

In some examples, the RF coil 12 in the RF coil assembly 10 can be used for magnetic resonance imaging, such as by receiving magnetic resonance signals or transmitting $B_1$ fields for the excitation or other manipulation of nuclear spins. In some other examples, the RF coil 12 in the RF coil assembly 10 can be used to provide electrostimulation or functional stimulation.

In configurations where the connecting element 18 is a wired connector that communicates signals between the RF coil 12 and the RF controller 20, the wired connector may be an electrical connector or a fiber optic connector. Examples of electrical connectors include conductive wires and coaxial cables, among others.

When the connecting element 18 is a wired connector that operatively engages the RF coil 12, the connecting element 18 can be permanently coupled to the RF coil 12, or can be removably coupled to the RF coil 12. In the latter construction, the connecting element 18 can removably couple to the RF coil 12 via an appropriate electrical connection (e.g., a plug) or optical connection (e.g., a fiber optic connector). Such a connection can be provided adjacent the RF coil 12, or distal to the RF coil 12 along a length of the connecting element 18.

Figure 2B:
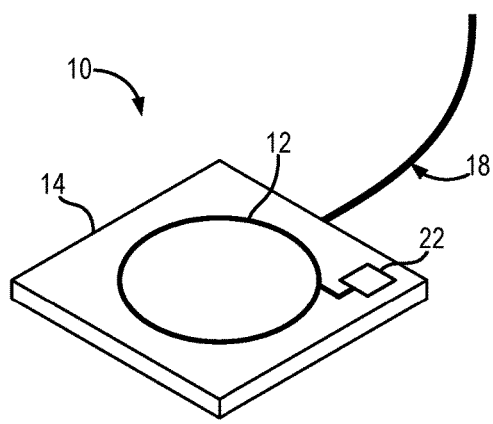
FIG. 2B shows another example of an RF coil assembly that implements a wireless RF coil.

In another example shown in FIG. 2B, the connecting element 18 does not operatively engage the RF coil 12, and is instead coupled to the absorbent member 14. In these configurations, the connecting element 18 may be a sterilized string, or the like. Because the connecting element 18 does not communicate signals between the RF coil 12 and the RF controller 20 in these examples, the RF coil 12 may be a wireless RF coil that wirelessly communicates signals between the RF coil 12 and the RF controller 20. In these configurations, a wireless controller 22 that contains the electronics or circuits that facilitate communication between the RF coil 12 and the RF controller 20 is provided on the absorbent member 14.

A tracking marker can be incorporated into the RF coil assembly 10 to provide tracking of the RF coil assembly 10 during an intraoperative procedure (e.g., via surgical navigation or surgical guidance). The marker may be an optical marker that can be visualized and tracked with an optical tracking system, an x-ray opaque marker that can be visualized and tracked with an x-ray imaging system, an RF emitter that can be visualized and tracked via an emitted RF signal, among others. The RF coil assembly 10 can include any one or combinations of such tracking markers. The tracking marker can be coupled to the absorbent member 14, or at or near the end of the connecting element 18 adjacent the absorbent member 14.

While in some examples the RF coil assembly 10 can include a tracking marker, such as an RF emitter, for electromagnetic navigation or guidance, in some other examples, the RF coil 12 of the RF coil assembly 10 can be used to provide electromagnetic-based tracking of the RF coil assembly 10 for navigation or guidance.

In some instances, the tracking marker can include an x-ray opaque marker such that x-ray imaging of the subject or patient, whether during an intraoperative procedure or after the completion of such a procedure can be used to provide additional verification that an RF coil assembly 10 has not been unintentionally left in a subject or patient.

Figure 2C:
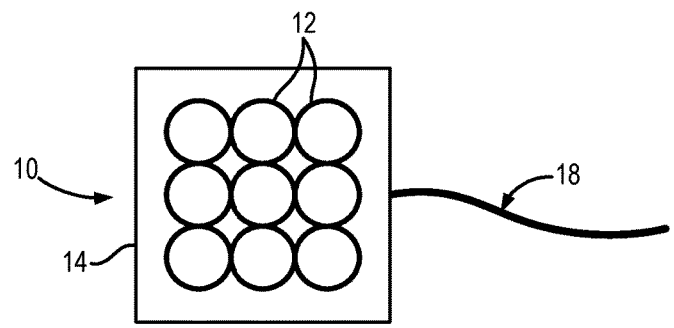
FIG. 2C shows another example of an RF coil assembly that implements a plurality of RF coils to provide for imaging over a larger region-of-interest.

It will be appreciated that while the RF coil assembly 10 can include a single RF coil, as shown in FIGS. 2A and 2C, the RF coil assembly 10 can also be constructed to include a plurality of RF coils to provide for imaging over a larger region-of-interest, as shown in FIG. 2C. In these instances, the plurality of RF coils can be connected in series, or as otherwise may be suitable for the application at hand. The absorbent member 14 is then sized to accommodate the plurality of RF coils. In these configurations, the RF coils can be arranged in a regular array (e.g., a square array, rectangular array, circular array, or other shaped array).

Figure 3A:
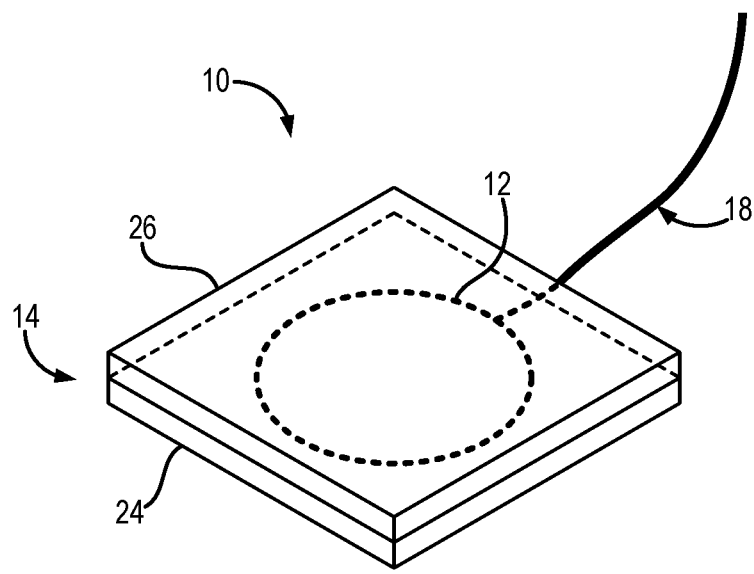
FIG. 3A shows an example of a layered construction of an RF coil assembly.
Figure 3B:
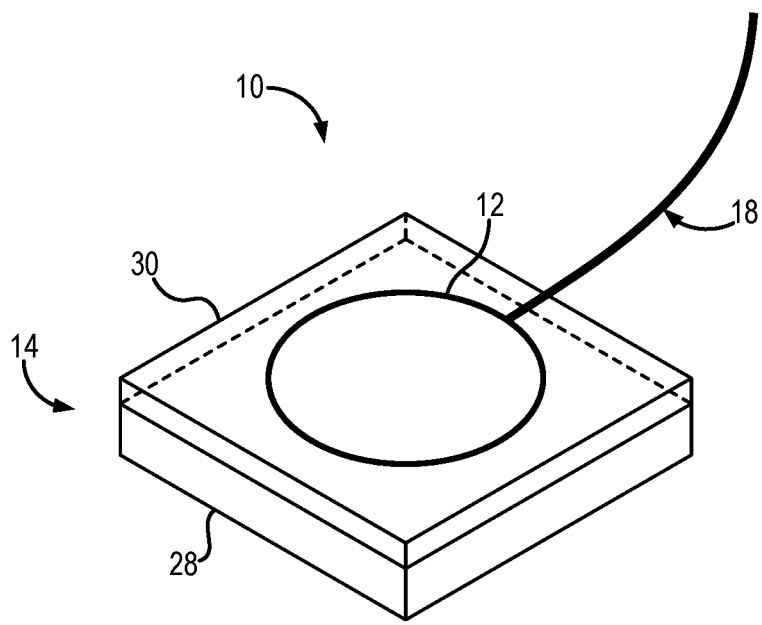
FIG. 3B shows another example of a layered construction of an RF coil assembly.

As shown in FIGS. 3A and 3B, the absorbent member 14 may include multiple layers. For instance, as shown in FIG. 3A, the absorbent member 14 can include a first absorbent layer 24 and a second absorbent layer 26 both composed of an absorbent material. In these configurations, the RF coil 12 can be disposed between the first absorbent layer 24 and the second absorbent layer 26. The first absorbent layer 24 and second absorbent layer 26 can be composed of the same absorbent material, or may be composed of different absorbent materials, and the first absorbent layer 24 and second absorbent layer 26 can have similar thicknesses or different thicknesses.

In other configurations, the absorbent member 14 can include an absorbent layer 28 and a non-absorbent layer 30. The non-absorbent layer 30 can be composed of a suitable non-absorbent material, which may be a biocompatible material, such as polyurethane, polycarbonate, or polytetrafluoroethylene ("PTFE"), such as Teflon. In some configurations, the RF coil 12 can be disposed between the absorbent layer 28 and the non-absorbent layer 30. The non-absorbent layer 30 can thus provide a protective barrier for the RF coil 12. The RF coil 12 can also be coupled to the non-absorbent layer 30, whether on the surface facing the absorbent layer 28 or the externally facing surface of the non-absorbent layer, as shown in FIG. 3B. In both instances, the non-absorbent layer 30 can provide a more robust substrate for the RF coil 12. In some constructions, the non-absorbent layer 30 is composed of a dielectric material to provide a dielectric substrate for the RF coil 12. The absorbent layer 28 and the non-absorbent layer 30 can have similar thicknesses, or as shown in FIG. 3B, the absorbent layer 28 can be thicker than the non-absorbent layer 30. Both the absorbent layer 28 and the non-absorbent layer should be sufficiently flexible so as to conform to the surface of tissue to which the RF coil assembly 10 is provided; however, in some configurations the non-absorbent layer 30 can be more rigid than the absorbent layer 28.

In still other configurations, the RF coil assembly 10 can include two or more layers. In some implementations, each layer can have a separate RF coil 12 coupled to it. For instance, as will be described below, an RF coil assembly 10 may have two layers where the first layer has a first array of stripline coil elements coupled thereto, and the second layer has a second array of stripline coil elements coupled thereto. In this example construction, the striplines can be arranged perpendicular to each other, such that they correspond to different regions of sensitivity.

As mentioned above, the RF coil assemblies 10 described in the present disclosure may be employed for local imaging during an intraoperative procedure, such as an open craniotomy, spinal surgery, other neurosurgical or intraoperative neurological procedures, or intraoperative procedures involving other anatomical regions. In some intraoperative procedures, the RF coil assemblies 10 can be provided for endoscopic use, such as by providing the RF coil assemblies 10 endonasally, endorectally (e.g., for imaging the prostate), or the like. The RF coil assembly 10 may also be used to examine tissue samples (e.g., ex vivo tissue samples).

As described above, in some embodiments, the electrical and imaging components for operating the RF coil assembly 10 may be divided into two groups: components that are coupled to or otherwise provided on or adjacent the absorbent member 14, and components that are housed distal to the absorbent member 14, such as in or along the connecting element 18 or in the RF controller 20. In some embodiments, at least some of the electrical components are housed within the RF controller 20, while other components, such as other electrical components and imaging elements or imaging assemblies, are coupled or otherwise provided to or adjacent the disposable body portion of the RF coil assembly 10 (e.g., the RF coil 12 and absorbent member 14). For example, at least some of the electrical components, such as at least some components of the tuning and matching circuit, or preamplifier circuit, may be housed within the RF controller 20.

Some example configurations for the integration of electrical components into the RF coil assembly 10 and RF controller 20 are as follows. In one example, only the wire portion of the RF coil 12 is coupled to the absorbent member 14 of the RF coil assembly. In another example, the wire portion of the RF coil 12 and tuning capacitors are coupled or otherwise provided to or adjacent the absorbent member 14, while the matching components and preamplifier(s) reside in the RF controller 20. In another example, the wire portion of the RF coil 12, tuning capacitors, and matching circuits are coupled or otherwise provided to or adjacent the absorbent member 14, while the preamplifier(s) reside within the RF controller 20. Finally, in another example, all components may be coupled or otherwise provided to or adjacent the absorbent member 14. In embodiments in which one or more components are integrated into the RF controller 20, for use with a disposable RF coil assembly 10 having one or more integrated RF coils 12, the tolerances on the capacitors housed within the RF controller 20 could be specified to be sufficiently low or tight.

Figure 4:
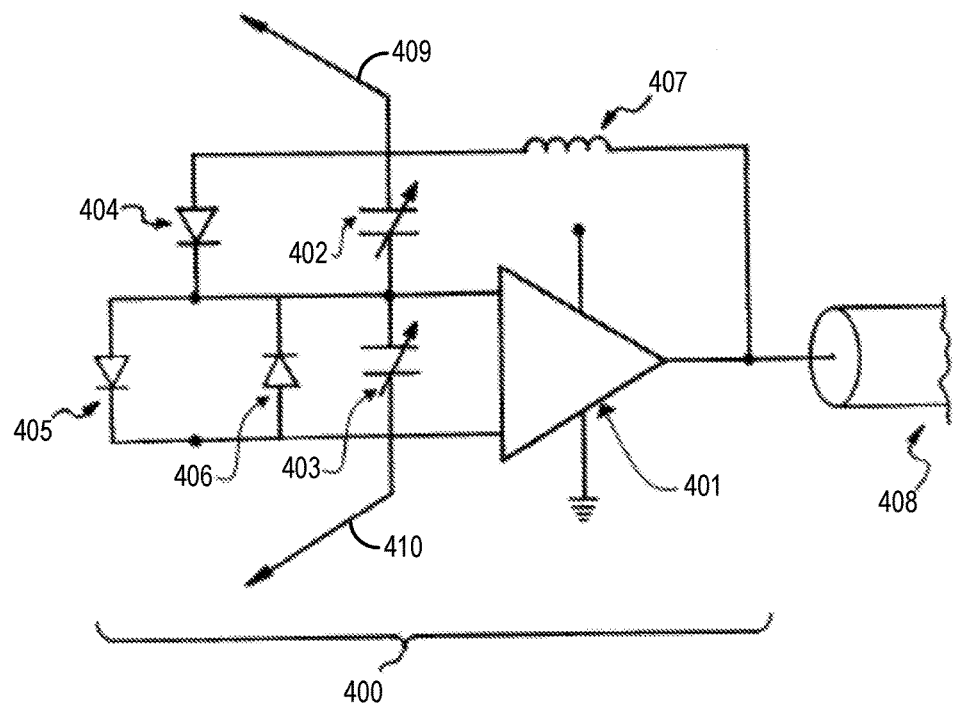
FIG. 4 shows an example circuit for receiving signals from a magnetic resonance coil element.

FIG. 4 schematically illustrates an example implementation of a circuit for receiving signals from a magnetic resonance coil element, such as an RF coil 12, within an RF coil assembly 10. The electrical circuit 400 includes a preamplifier 401 (or low noise amplifier ("LNA")) that amplifies the signal that is generated. Variable capacitors (402 and 403) are used to tune and match the circuit 400. Diodes (404, 405, 406) are used to detune the coil (if it is a receive only coil) when the system is transmitting. One or more inductors (or RF chokes) 407 are used to separate DC control signals from the RF path.

In the example circuit 400 for receiving signals from an RF coil shown in FIG. 4, a coil element (e.g. a single coil or a coil element of an array of coil elements) is connected and matched to a preamplifier 401, which will amplify the received signal for processing. These channels may be connected using a 50Ω coaxial cable 408 that carries the AC signal to and from the preamplifier 401. The preamplifier 401, itself, may be powered through a set of discrete wires. In this diagram, the coil is connected to the two arrows 409 and 410. A coax connection could be made here with the outside of the connector at the bottom (410) and the center line at the top (409). Alternatively, a pair of wires could be used, or a twinax line, or a twisted pair, or a direct connection to the coil.

The circuit 400 may contain an active and passive detuning diode to ensure the coil is non-resonant at the Larmor frequency during the transmission phase of an MRI scan. The passive diode is activated by the transmitting field while the active diode is powered through the centerline of the aforementioned coaxial cable.

The coil is tuned to the resonant frequency of the system. A variable capacitor is typically used for this purpose because it is easily adjusted. However, a fixed capacitor could alternatively be used. Secondly, to achieve the lowest noise figure, the preamplifier 401 preferably has an ideal source impedance. Another variable capacitor can be used to vary the source impedance so that this impedance is achieved. Again, a fixed-value capacitor could be used for this purpose. The inductor 407 is used to as an RF choke to separate the control signals (e.g., a command to block during transmit) from the RF path.

As described above, the components in the circuit 400 can reside on or near the absorbent member 14, in the RF controller 20, or can be divided between the two locations.

It is noted that the circuit 400 shown in FIG. 4 is but one example circuit. There are alternate methods to noise match the preamplifier (e.g., using inductors, multiple capacitors, multiple inductors, transformers, transmission lines), alternate methods to detune the coil (e.g., PIN diodes, switches, FETs, MEMS devices), and alternate methods to shield the control signals from the RF line (e.g., PIN diodes, switches, transmission lines).

Although FIG. 4 illustrates a single circuit that is connectable to a single coil, it will be understood that in embodiments in which the RF coil assembly 10 includes an array of coil elements (i.e., multiple channels), or where multiple RF coil assemblies 10 are collectively used to form an array of coil elements, the circuit shown in FIG. 4 (or an alternative circuit) may be included for each coil element in the array. For instance, as mentioned above, the RF coil assembly 10 may be constructed to include an array of RF coils to provide imaging over a larger region-of-interest.

Some RF coil assembly designs according to embodiments described in the present disclosure serve to transmit or receive a $B_1$ field that is oriented substantially perpendicular to the main magnetic field (i.e., the $B_0$ field) as generated by the main magnet, which maximizes or otherwise increases the potential to transmit energy to or receive signals from nuclear spins. It is possible that the alignment of the RF coil 12 in the RF coil assembly 10 with the main magnetic field will change with operating conditions (e.g., depending on the contour of the tissues to which the RF coil assembly 10 is positioned adjacent). For this reason, the RF coil 12 may be made available in varying coil geometries to accommodate operating conditions and magnetic field orientations. The various coil configurations described below provide several non-limiting example implementations of such different coil geometries.

The coil designs presented below are provided as example and non-limiting implementations of potential coil configurations that can be used for the RF coil 12 in the RF coil assembly 10 described in the present disclosure. Some of the following examples provide RF coils that are configured to produce a forward-looking focused receiving or transmitting zone. In other words, some of the following examples provide RF coil configurations that are sensitive to regions anterior to the tissue-facing surface of the RF coil assembly 10. These examples may be included or incorporated within the RF coil assembly 10 described in the present disclosure.

The coils themselves may be formed from a conductive material, for example copper, silver, silver coated copper wire, super conducting wire or tape, high temperature superconducting wire or tape, carbon nanotubes, or graphene, that may or may not be cooled (e.g., to lower metal resistivity and hence increase SNR) during image acquisition or RF transmission. Where needed or otherwise desired, a dielectric substrate may be used, as mentioned above. Suitable dielectric materials may include materials such as polyurethane, polycarbonate, Teflon, air, foam, FR-4, a liquid crystal polymer ("LCP"), a low temperature co-fired ceramic ("LTCC"), or a high temperature co-fired ceramic ("HTCC"), among others.

It will be understood that the RF coil 12 may be provided according to a number of different configurations and fabrication methods. For example, the RF coil 12 may be formed from wire and wound. Alternatively, the RF coil 12 could be thick film conductor, and screen printed. In other examples, the RF coil 12 could be conductive tape and adhered to a surface. In other examples, the RF coil 12 can be constructed of metal that may be sputtered or machined away from a block of metal, etched, or formed using electrical discharge machining ("EDM").

Loop Coils

FIGS. 5A-5D illustrate various example implementations of a loop coil. The loop coil may be beneficial given its high Q, accompanying high SNR, and versatility.

Figure 5A:
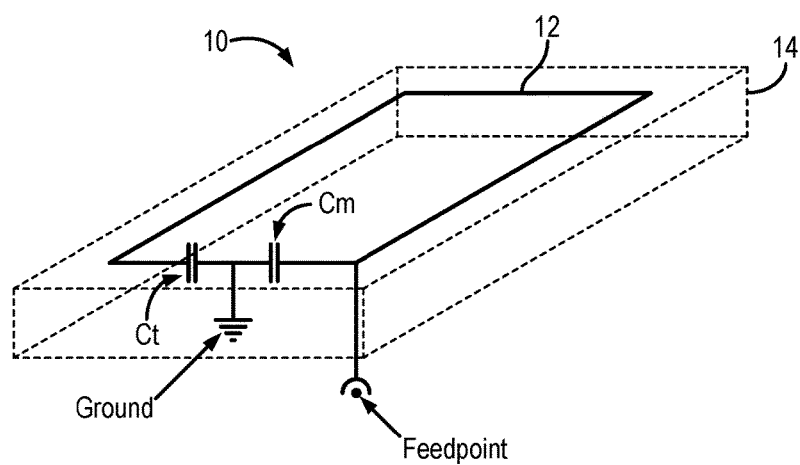
FIG. 5A shows an example of an RF coil assembly that implements a loop coil.

In FIG. 5A, a loop coil is oriented to be coplanar with a surface of the absorbent member 14. The feeding location is generally indicated at the location of the semi-circle. Two capacitors (Ct and Cm) are used to tune the loop to the appropriate resonant frequency. Not shown are any additional matching components that would be used to noise match the loop to a preamplifier. Also not shown are any preamplifiers which could be located separately (or, alternatively, formed within the RF coil assembly 10). The feedpoint is located across Cm.

Figure 5B:
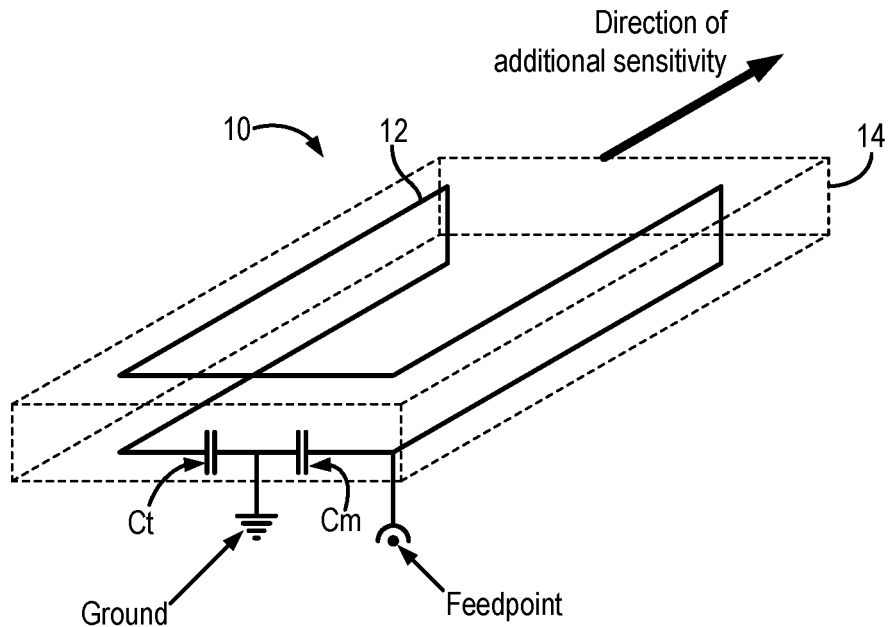
FIG. 5B shows an example of an RF coil assembly that implements a folded loop coil.

In FIG. 5B, a folded loop locates the fold at one edge of the absorbent member 14 to provide for additional sensitivity of the RF coil 12 along the direction indicated in the figure. Two capacitors (Ct and Cm) are used to tune the loop to the appropriate resonant frequency. Not shown are any additional matching components that would be used to noise match the loop to a preamplifier. Also not shown are any preamplifiers which could be located separately (or, alternatively, formed within the probe). The feedpoint is located across Cm.

Figure 5C:
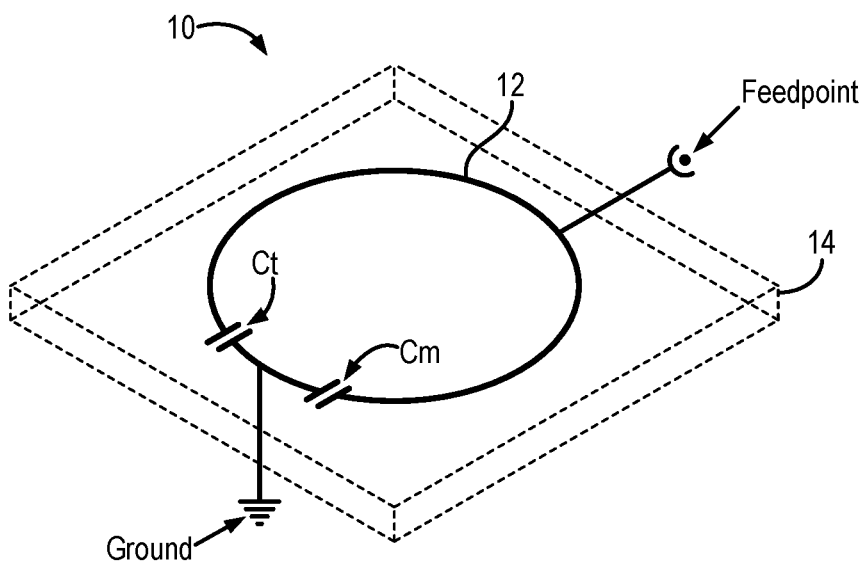
FIG. 5C shows an example of an RF coil assembly that implements a circular loop coil.

The loop coil may also be shaped as a circular loop, as in FIG. 5C. This loop could have varying diameters to increase the intensity of the forward-looking sensitive region of the coil. The diameter of the loop may range from micrometers to centimeters. The loop coil may be constructed from conducting material, as previously described, and may be backed by a dielectric substrate. In FIG. 5C, the loop is tuned with capacitive elements (such as Cm and Ct), and is fed across capacitor Cm. Not shown are any preamplifiers which could be located separately (or, alternatively, formed within the probe).

Loop coils may be used in an array, and may be decoupled from other elements within the array either geometrically or with capacitive or inductive components.

Figure 5D:
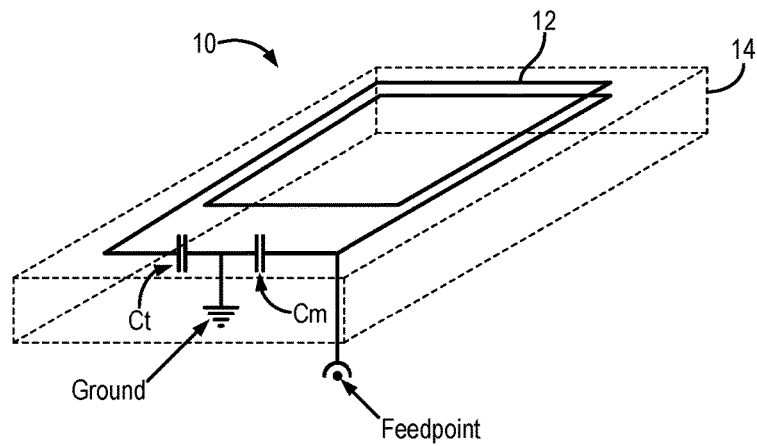
FIG. 5D shows an example of an RF coil assembly that implements a loop coil with multiple turns.

FIG. 5D shows a two-turn coil, oriented to be coplanar with a tissue-facing surface of the absorbent member 14. The two-turn loop coil uses capacitors Cm and Ct to tune the coil to the resonant frequency of the system. The feedpoint is located across capacitor Cm. Not shown are any preamplifiers which could be located separately (or, alternatively, formed within the probe). It will be understood that in alternate embodiments, any number of turns may be employed.

Figure 6A:
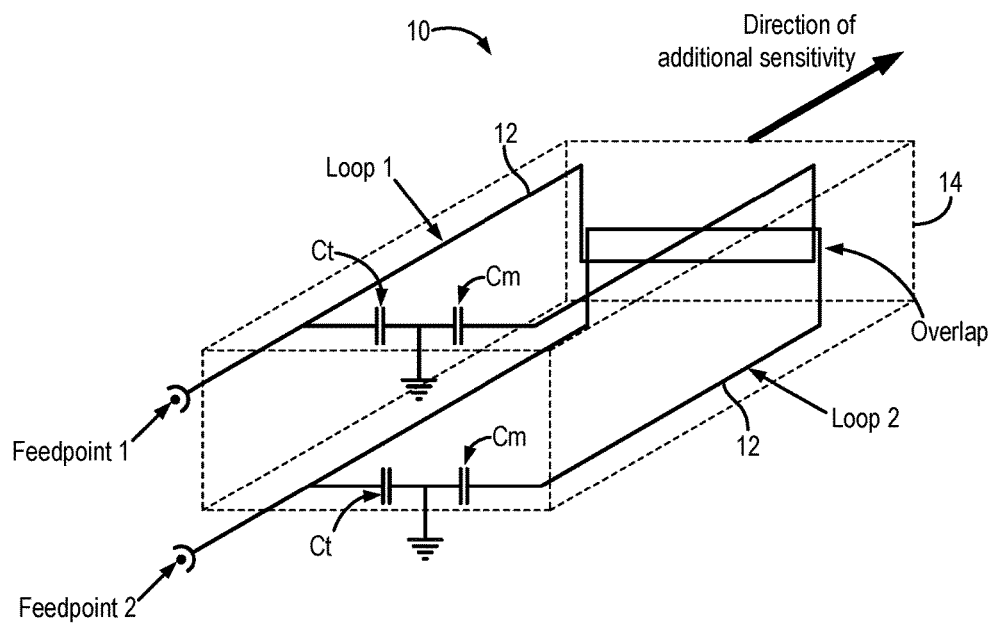
FIG. 6A shows an example of an RF coil assembly that implements two folded loop coils that partially overlap to provide additional directional sensitivity.
Figure 6B:
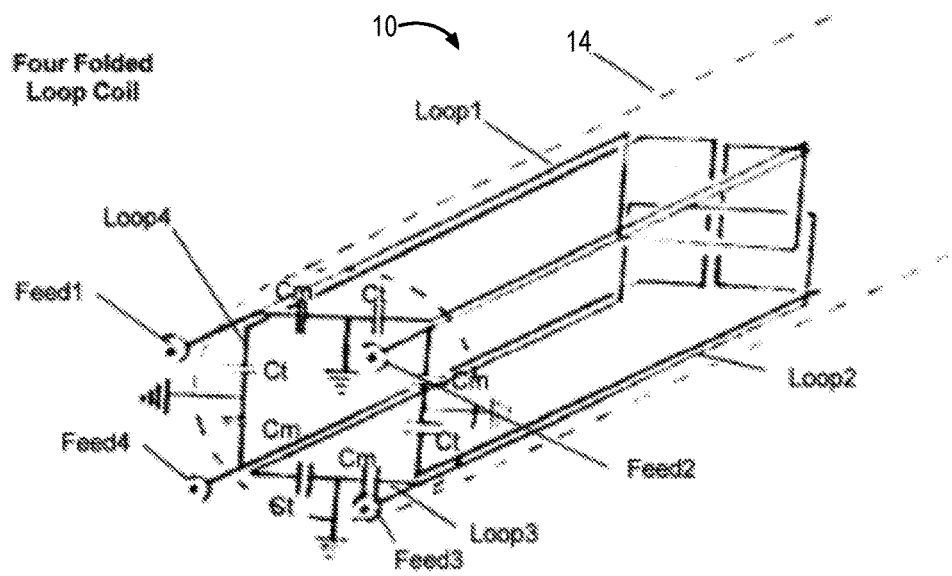
FIG. 6B shows an example of an RF coil assembly that implements four folded loop coils that partially overlap in a region to provide additional directional sensitivity.

FIGS. 6A-6B illustrate example coil loop implementations involving two fold loop coils (FIG. 6A) and four folded loop coils (FIG. 6B) that are provided at or near one side of the absorbent member 14 in order to enhance the sensitivity of the RF coil 12 in that direction. These constructions may be useful for an absorbent member 14 such as a sponge or other such form.

In FIG. 6A, two folded loops are arranged so that their folds are located at one side of the absorbent member 14 to provide additional outward facing sensitivity at that side of the absorbent member 14. The two loops are overlapped so as to cancel their mutual inductance to decouple the two loops. There is no electrical connection made at the overlap. It is also understood that in alternate embodiments, capacitors of inductors could be used to decouple the loops. Each of the loops is equipped with a pair of capacitors for tuning and a feeding location. Not shown are any noise matching circuits, or any decoupling diodes, or any preamplifiers that might be used to amplify the signal. The feedpoints for each loop are located across capacitor Cm.

FIG. 6B is similar to FIG. 6A, except that the RF coil 12 in FIG. 6B includes four loops instead of two. Again, all loops are overlapped to decouple them, without forming an electrical connection. As in FIG. 6A, other decoupling methods are possible, such as using shared capacitors, or inductors. Each loop is equipped with a pair of capacitors for tuning as well as a feeding location. Not shown are any noise matching circuits, or any decoupling diodes, or any preamplifiers that might be used to amplify the signal. The folded ends are located at one side of the absorbent member 14, which may be the distal end of an elongate sponge.

Butterfly Coils

In some embodiments, one or more coils of the RF coil assembly 10 may be provided in a butterfly coil configuration. For example, butterfly coils may be coupled to or otherwise provided within the absorbent member 14 in a planar configuration or in a folded configuration (to improve the sideward-looking imaging aspects of the coil). Example implementations of butterfly coil configurations are, shown in FIGS. 7A-7C.

Figure 7A:
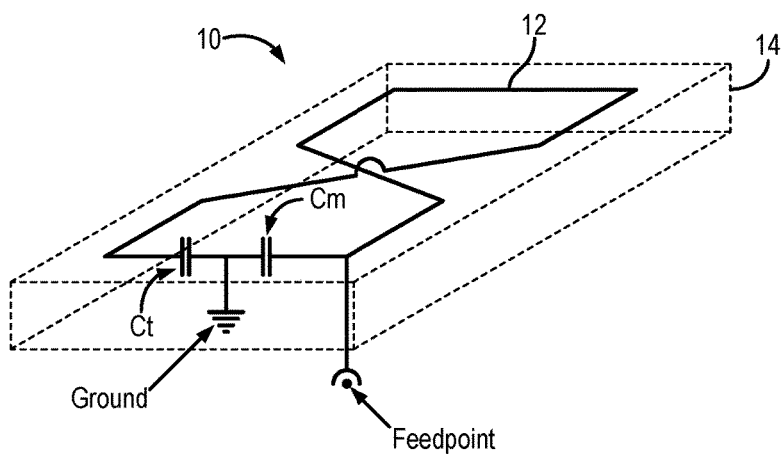
FIG. 7A shows an example of an RF coil assembly that implements a butterfly coil.

FIG. 7A shows a butterfly, or figure-eight, coil. Here, the RF coil 12 is shown coplanar with a tissue-facing surface of the absorbent member 14. Two capacitors, Cm and Ct, are used for tuning the coil to the appropriate resonant frequency, and the feeding location is indicated by the semicircle. This coil will be sensitive to areas above and below it. Not shown are any noise matching components, control signals, detuning elements, or preamplifiers.

Figure 7B:
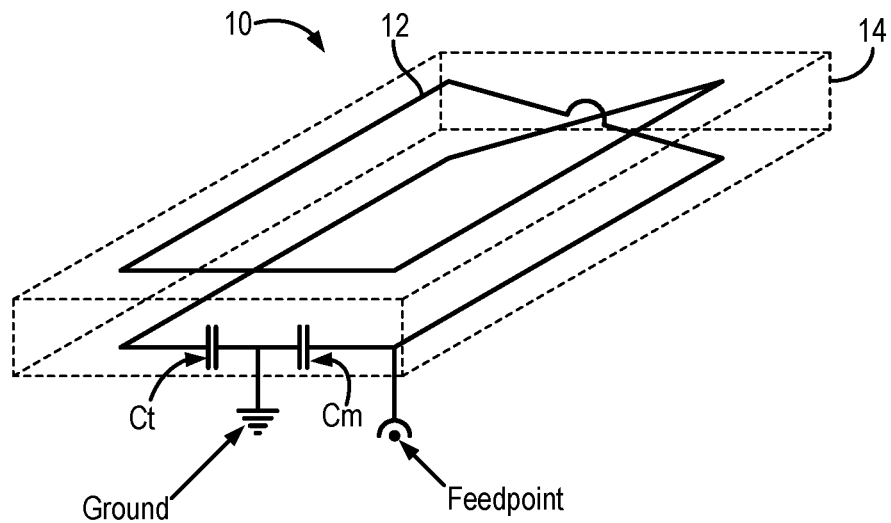
FIG. 7B shows an example of an RF coil assembly that implements a folded butterfly coil.

FIG. 7B also shows a folded butterfly coil. The fold is located at one end (or side) of the absorbent member 14 to provide additional sensitivity along a direction extending outward from that side (or end) of the absorbent member 14. No electrical connection is made at the fold location. Two capacitors, Cm and Ct, are used for tuning the coil to the appropriate resonant frequency, and the feeding location is indicated by the semicircle. Not shown are any noise matching components, control signals, detuning elements, or preamplifiers.

Figure 7C:
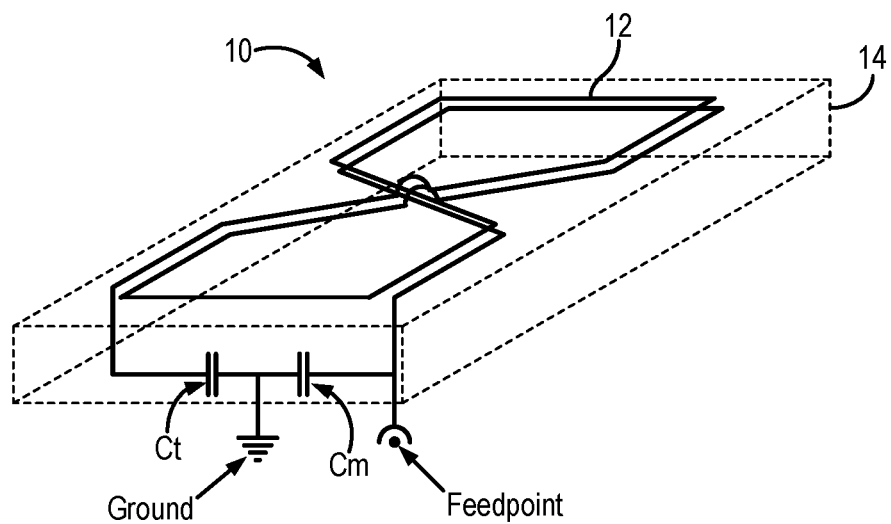
FIG. 7C shows an example of an RF coil assembly that implements a butterfly coil with multiple turns.

FIG. 7C shows a butterfly coil with two turns of wire. Two capacitors, Cm and Ct, are used for tuning the coil to the appropriate resonant frequency, and the feeding location is indicated by the semicircle. This coil will be sensitive to areas above and below it. Not shown are any noise matching components, control signals, detuning elements, or preamplifiers. No electrical connection is made between the two turns of the coil, save through the capacitors Cm and Ct.

As with other coil geometries described here, the coil dimensions may be scaled from micrometers to centimeters (e.g., from approximately 1 micron to approximately 1 cm) in diameter and micrometers to centimeters in length.

The butterfly coil may have any number of turns, and may be positioned along the length of the absorbent member 14, or where the absorbent member is cylindrical (e.g., a cylindrical sponge) the butterfly coil may be positioned radially surrounding the cylindrically shaped absorbent member 14, such that each butterfly is rotated around the axis that runs along the length of the cylindrically shaped absorbent member 14. The butterfly coil is constructed from a conducting material and may be formed upon a dielectric substrate as described above. The butterfly coil may be decoupled from other elements in a coil array through geometric positioning or capacitive/inductive elements.

Folded Stripline

Figure 8A:
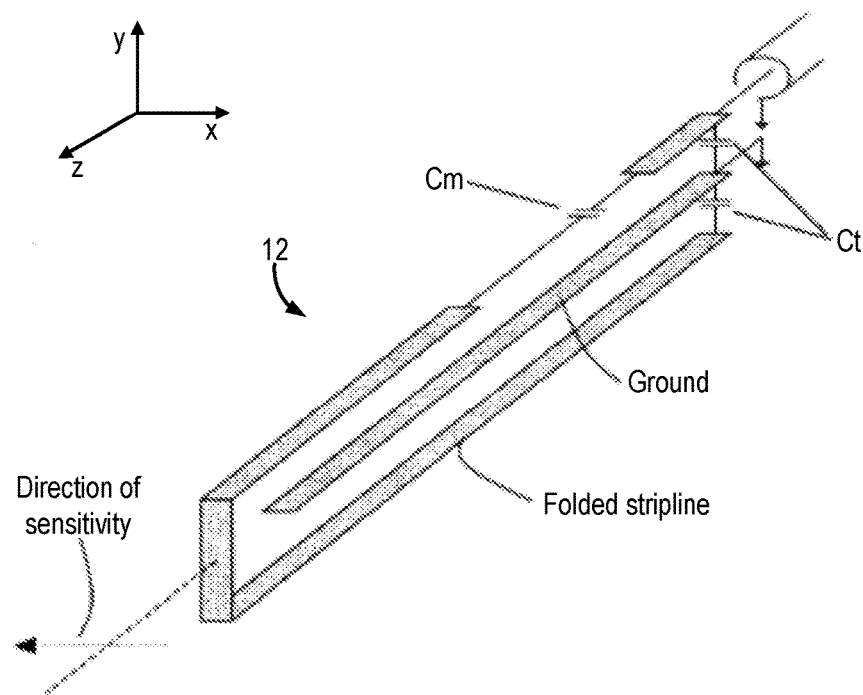
FIG. 8A shows an example of an RF coil assembly that implements a stripline coil.
Figure 8B:
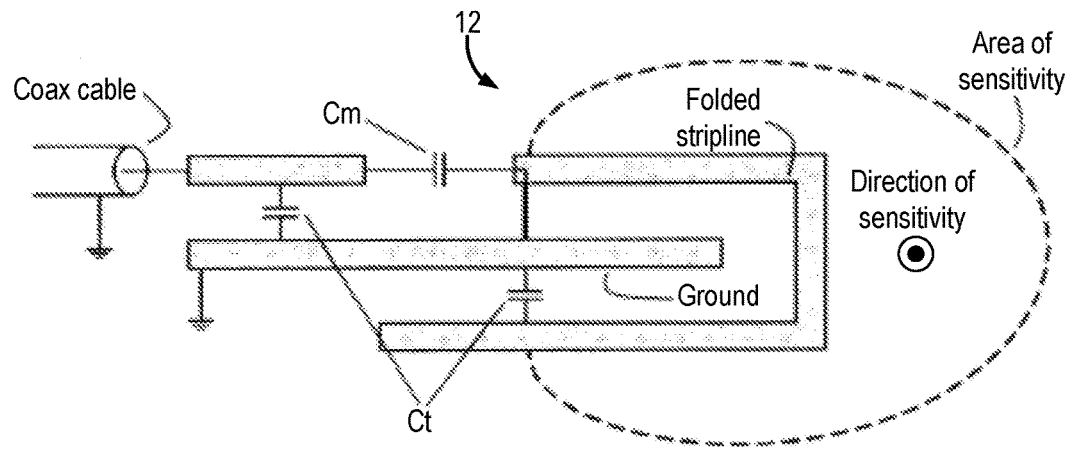
FIG. 8B shows an example configuration for feeding a folded stripline coil.
Figure 8C:
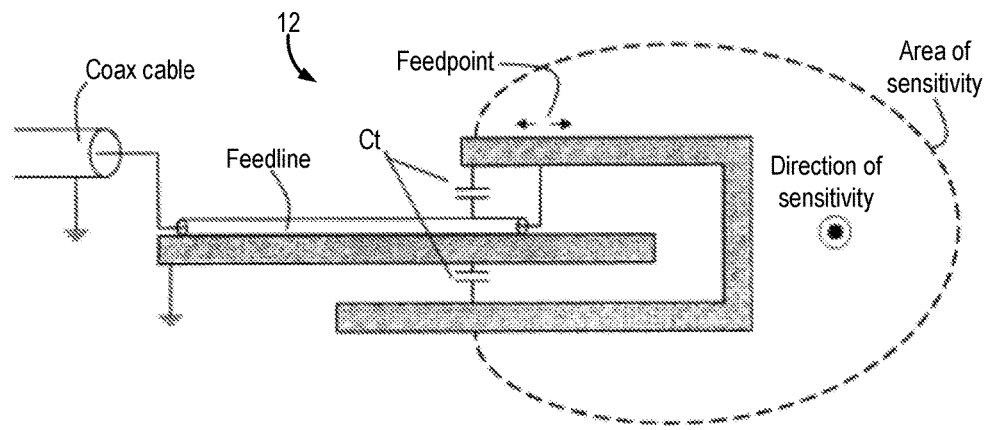
FIG. 8C shows another example configuration for feeding a stripline coil.

In another example, the RF coil 12 can be based on a stripline resonator, as illustrated in FIGS. 8A-8C. This stripline generates a $B_1$ field (or, as a receive-only coil, is sensitive to magnetic fields) in the x-direction. Thus, in general, the stripline coil can be arranged relative to the absorbent member 14 such that the x-direction is normal to the tissue-facing surface of the absorbent member 14. In this arrangement, the sensitivity of the stripline coil will coincide with the tissue-of-interest to be imaged.

The stripline, having a folded configuration, can also focus the imaging region in an end-fire direction (e.g., in a region beyond the distal extent of the coil, as shown in FIGS. 8B-8C. This configuration may be useful for imaging regions such as cavities or recesses, or for use in endonasal applications, among others.

As seen in FIG. 8A, this stripline coil is electrically shortened with capacitors (Ct) to a half-wavelength in dimension where the wavelength is akin to the aforementioned Larmor frequency. A matching capacitor (Cm) is used to match the stripline to the amplifier. This structure is advantageous given its low-profile design, and high adjacent SNR capability.

The stripline may be constructed from conducting material that is folded about a dielectric substrate containing a ground-plane, also made from conducting materials. The stripline may be this constructed to reside within the absorbent member 14, or such that the stripline extends around a periphery of the absorbent member 14.

The signal line and the ground line should be separated by some material, such as a dielectric, or other insulator, such as the absorbent material of the absorbent member 14. The dielectric can also be used to insulate the outer conductors from the patient. In this figure, the dielectric is between the conductors, as well as on the outside of the outer conductors. The RF coil 12 shown in FIG. 8A shows a side view of the stripline inside or otherwise coupled to an absorbent member 14 having an elongate shape, such as a cylindrical sponge.

In one example, the stripline can be fed using a series capacitor to match the feedline to 50Ω (or any desired impedance), as shown in FIGS. 8B and 8C. In another example, the stripline can be fed by varying the location of the feedpoint to achieve a 50Ω match (or any desired impedance) and does not use a matching capacitor (Cm). In this configuration, the outer conductor of a coax line may be (though is not required to be) electrically connected to the ground conductor of the RF coil 12 to avoid floating conductors when connecting the feedline.

It will be understood that any or all the electrical components (e.g., capacitors, diodes, amplifiers, RF inductors) from the conducting strips used for the stripline may be contained within the RF controller 20 described above. This configuration allows for a low-cost disposable construction to be provided, where the electrical components are located in a re-usable RF controller 20 and connected to a disposable RF coil 12 and absorbent member 14 of the RF coil assembly 10. A preamp could be located on or adjacent the absorbent member 14, or even further removed from the RF coil 12, such as in the RF controller 20. However, putting the preamp closer to the RF coil 12 can improve performance by increasing SNR.

In some example implementations, the width of the stripline can vary from less than approximately 1 mm to greater than 13 mm, while the length of the folded stripline can measure from less than 1 mm to greater than 100 mm. The value of the tuning capacitors Ct will change as the length is varied because the length of the antenna corresponds to inductance, and the capacitors are required to resonate with the inductance. One skilled in the art will know to vary the capacitor value as the length of the stripline is varied.

It will be understood that there are many possible configurations of the stripline resonator-based coil. The following sections illustrate some additional example implementations that involve coils based on multiple striplines.

Folded Quadrature Striplines

Figure 9:
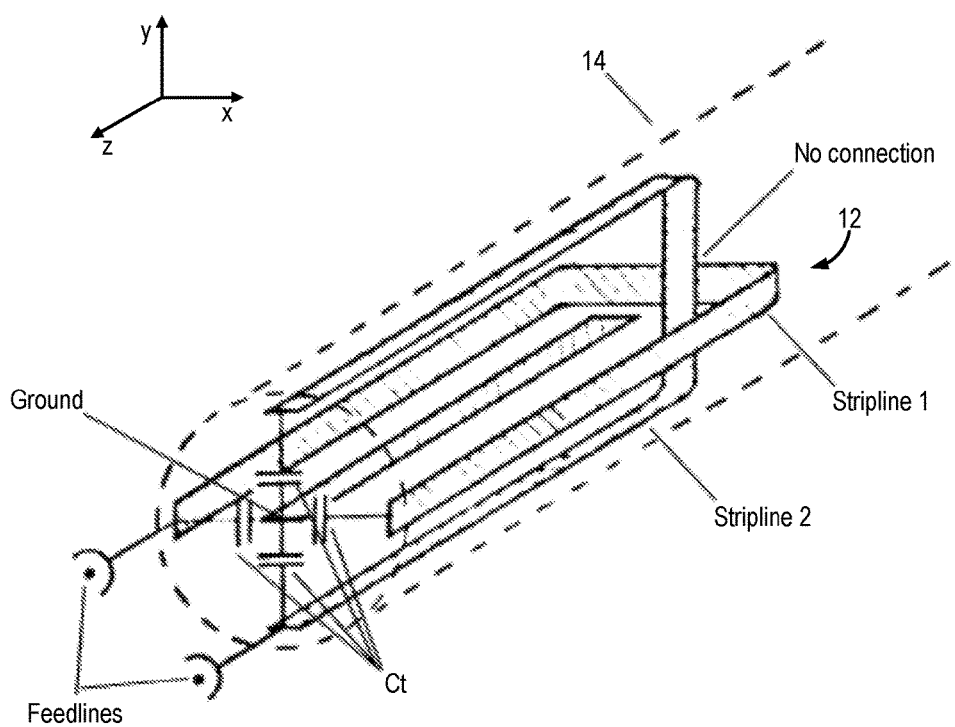
FIG. 9 shows an example of an RF coil assembly that implements two folded stripline coils.

A quadrature coil is sensitive to two orthogonal polarizations of magnetic field. FIG. 9 presents an example of two folded stripline coils as a quadrature pair. One of the striplines generates (or is sensitive to) a $B_1$ field in the x-direction and the other in the y-direction. The four capacitors shown in the figure are tuning capacitors. The center line is connected to ground. While the striplines both fold over each other at the distal end of the probe, there is no electrical connection made between the striplines at this point. The only electrical connection between the striplines is the common ground that they share.

To connect to tuning and matching circuitry, a ground connection can be attached to the center line. A matching circuit can be attached each of the circle-dot connections. The matching circuit could be a matching capacitor, or inductor, or phase shifting network, followed by a preamplifier.

It is to be understood that the number of striplines used herein may vary. These striplines are depicted as sharing a common ground plane within the center of the coil, however, in other embodiments, the striplines may have separate ground planes.

Stripline Arrays

Figure 10A:
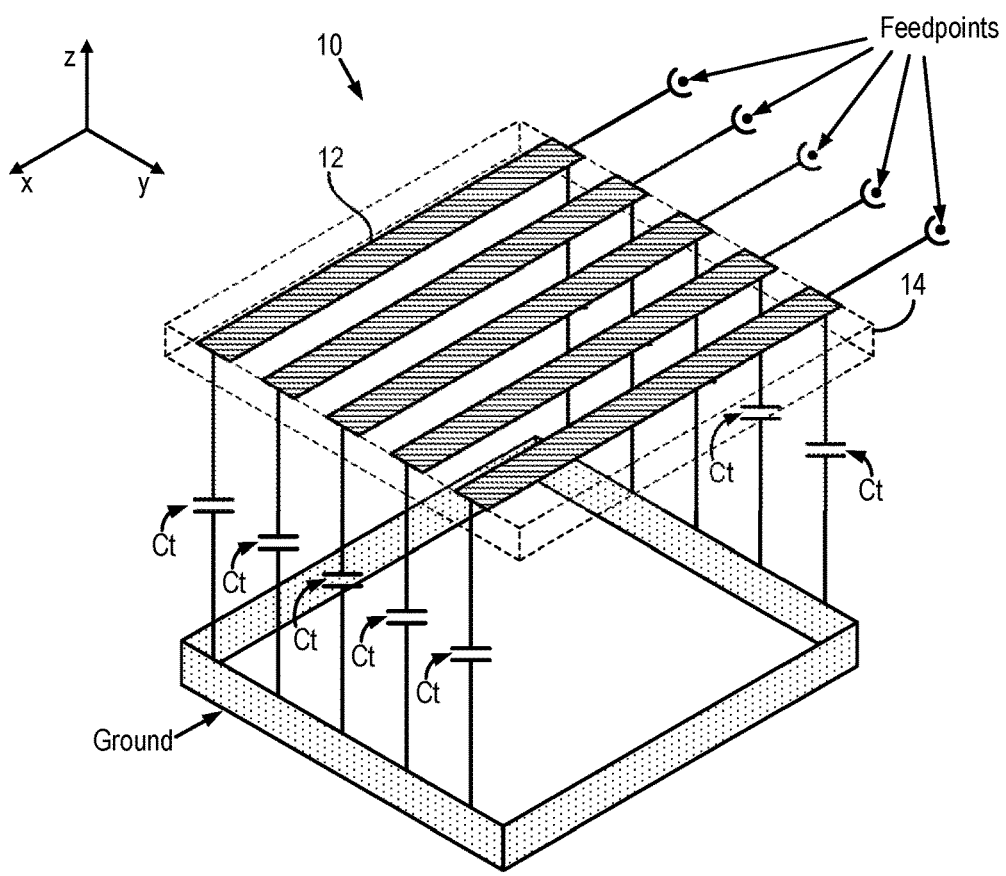
FIG. 10A shows an example of an RF coil assembly that implements an array of parallel stripline coils.
Figure 10B:
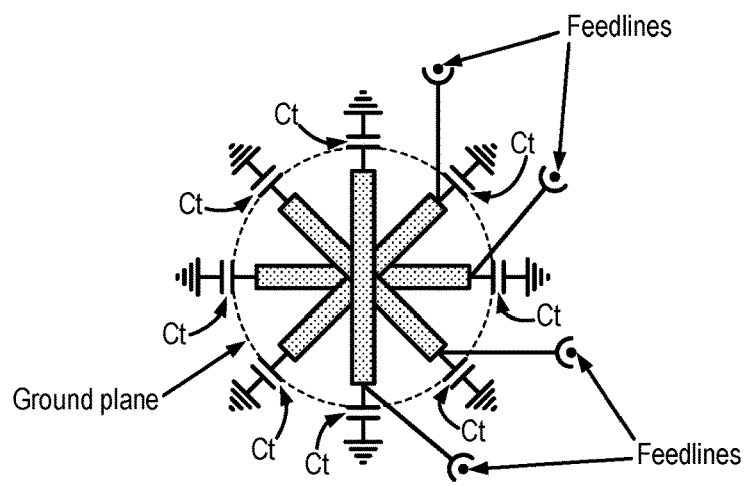
FIG. 10B shows an example of an RF coil assembly that implements an array of radially arranged stripline coils.

FIGS. 10A-10C illustrate examples where stripline resonators are provided in a coplanar arrangement with a tissue-facing surface of the absorbent member 14, either in a linear or radial formation. It will be appreciated that while the stripline are shown to be parallel with the x-direction (such that the sensitive direction is the y-direction), the striplines could also be aligned with the y-direction, such that the sensitive direction would then be the x-direction.

The common ground is a solid ground plane distal to each stripline, which may be located at or near the absorbent member 14. The depth is exaggerated in this figure to provide a clearer depiction of the components. The outputs can be combined as a phased array. In FIG. 10A the array of striplines is sensitive to a magnetic field in the y-direction. There are several possible methods (previously described) to feed striplines. In FIG. 10A, the feeding method is as per FIG. 8C. Preamplifiers and the remainder of the magnetic resonance imaging system are not shown.

In the radial arrangement, shown in FIG. 10B, the striplines are all above a common ground plane. In this example figure, four striplines are shown, each with a pair of tuning capacitors to adjust the resonant frequency. The striplines are not making electrical contact, and are separated vertically (i.e., through the plane of the drawing). The striplines are fed as per FIG. 8C. Again, not shown are preamplifiers or any further elements of a magnetic resonance imaging system. The output from each stripline are combined to form an image as a phased array coil.

Arrays

The preceding embodiments described several example implementations of coil configurations that may be employed in an intraoperative RF coil assembly according to the present disclosure. It will be understood that coils according to these configurations, or according to variations thereof, may be provided in an array form. It will also be appreciated that such arrays may be formed by multiple RF coil assemblies, each having one or more RF coils coupled thereto.

Sparse and Dense Arrays

In some embodiments, an array may be formed by providing, on or within an RF coil assembly, a plurality of coils in a prescribed spatial arrangement, or by providing a plurality of RF coil assemblies each having one or more RF coils in the prescribed spatial arrangement. The array of coil elements which combine to form a coil array may be provided according to many different embodiments without departing from the scope of the present disclosure. Example embodiments feature an array of RF elements to enable parallel imaging where the sensitivity of each element is used to accelerate imaging times. These arrays may be used as receive-only, transmit-only, or in combination as a transceiving device. In transceiving mode, an electrical switch is included in order to toggle between the receiving and transmitting circuits. Examples involving parallel imaging include implementing an asymmetric g-factor, reducing or eliminating phase encoding along one or more directions, and driving gradients in opposite direction.

Figure 11A:
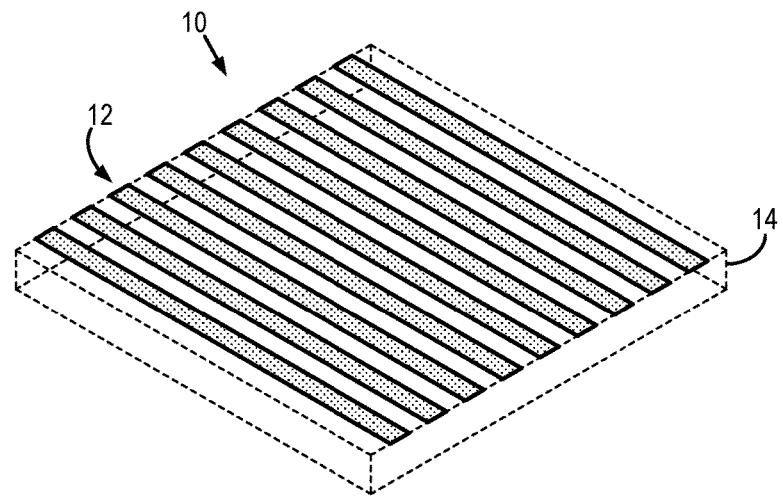
FIG. 11A shows an example of a dense array of stripline coils.

In some embodiments, the array may be a dense array (e.g., a high-density array) or a sparse array. As used herein, the phrase "dense array" refers to an array having a relative spacing between neighboring array elements of less than approximately 1 mm and the phrase "sparse array" refers to an array having a relative spacing between neighboring array elements of greater than approximately on the order of 1 cm. For example, FIG. 11A illustrates an example implementation of an RF coil assembly 10 having a dense array of stripline coil elements.

Figure 11B:
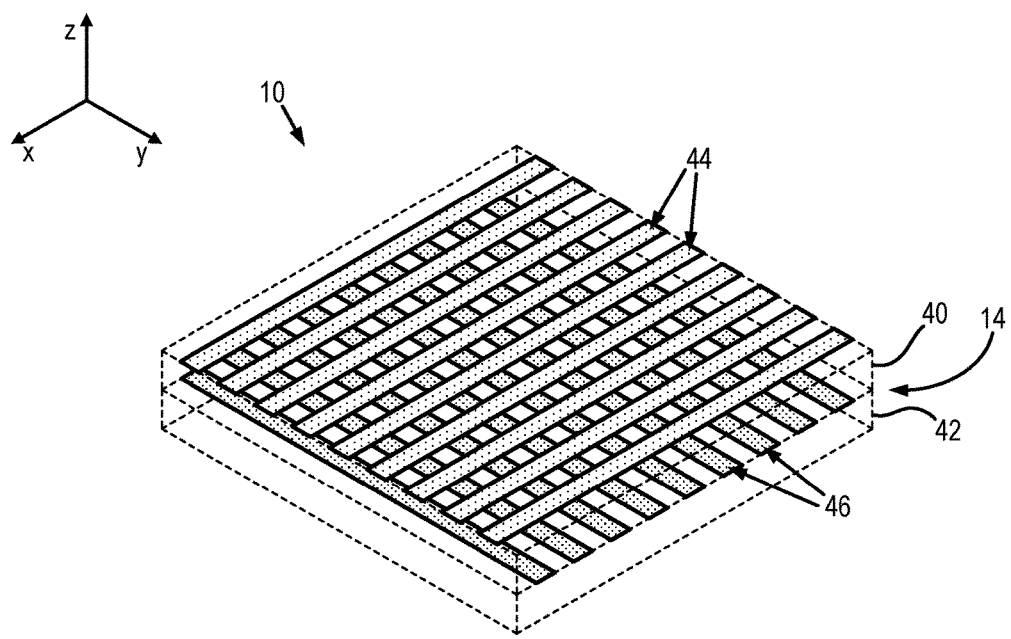
FIG. 11B shows an example of an RF coil assembly that implements two layers of perpendicularly arranged arrays of stripline coils.

As mentioned above, the RF coil assembly 10 can include an absorbent member 14 having multiple different layers, and in some instances can have a different RF coil 12 coupled to different ones of the layers. FIG. 11B illustrates an example of such a construction, in which an RF coil assembly 10 is seen as having an absorbent member 14 with at least a first layer 40 and a second layer 42. On the first layer 40, an array of stripline coil elements 44 is coupled, such that the striplines extend along the x-direction. On the second layer 42, an array of stripline coil elements 46 is coupled, such that the striplines extend along the y-direction. With this construction, the RF coil assembly 10 includes an RF coil 12 composed of the two arrays of stripline coil elements (44, 46), which provides sensitivity in both the x-direction (from coil array 46) and in the y-direction (from coil array 44).

In some embodiments, the array elements of a dense array may form a phased array. In a phased array, each coil has a spatially separate region of sensitivity.

Within the array, each element may be tuned to the Larmor frequency of the nuclei under investigation using non-magnetic capacitive components. These elements may have multiple tunings to enable collecting data from numerous nuclei. The desired tuning can be selected actively by way of an electronic switch that includes the appropriate tuning capacitors within the circuit, such as via the RF controller 20. The Larmor frequency is proportional to the applied magnetic field strength, and as such, the coil array can be designed to operate at varying field strengths, whether it be a low-field or high-field application. To maintain isolation between the channels corresponding to various coil elements, the coil elements can be decoupled from each other, for example, either capacitively, geometrically, or inductively within the circuit. The number and placement of the capacitive and/or inductive elements are dictated by individual coil geometries. Where appropriate, these components may be placed on the absorbent member 14 (i.e., on the disposable portion of the RF coil assembly).

In some embodiments, the RF coil assembly 10 may include a dense array of MRI receiver coils, such as an array of stripline coils, an array of multiple loop coils, among others. In this manner, a forward-looking region (e.g., a region coplanar with the tissue-facing surface of the absorbent member 14) can be imaged, for example, with a high sensitivity, and with the ability to cover the field of imaging using many small array elements, which enables parallel imaging.

Combinations of Different Coil Configurations and Geometries

In addition to the aforementioned embodiments involving single and multiple coils of a given type, it will be understood that in other embodiments, an RF coil assembly 10 may include multiple coil types, for example, to form a coil array.

For example, in some embodiments, two or more of loop coils, striplines, and butterfly coils can be combined within a given RF coil assembly 10. In some embodiments, the coils that are combined may include one or more folded coils to generate a focused sensitivity region. The proceeding section presents several non-limiting examples of such combinations. It will be understood that these examples are non-limiting and that other configurations may be obtained by alternative combinations of two or more coil types.

Figures 12A, 12B, 12C:
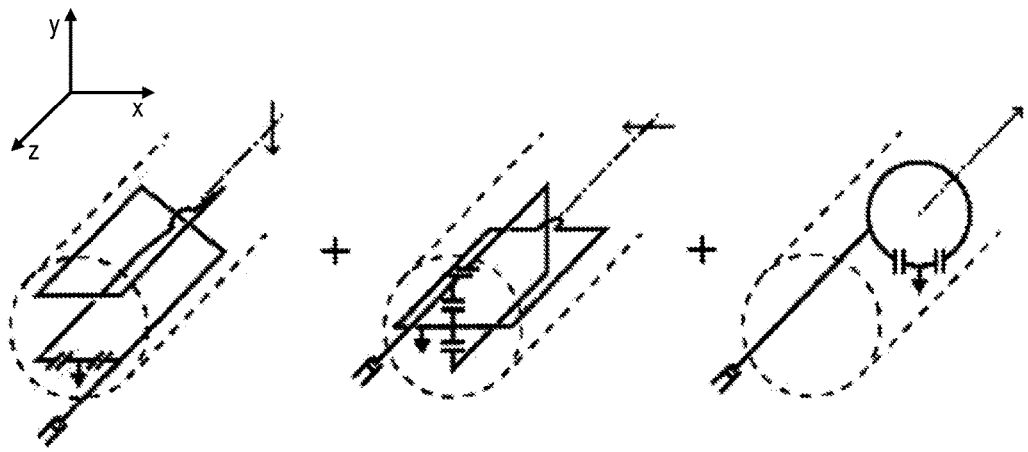
FIGS. 12A-12C show examples of multiple different coil geometries that can be combined in a single RF coil assembly.
Figures 13A, 13B, 13C:
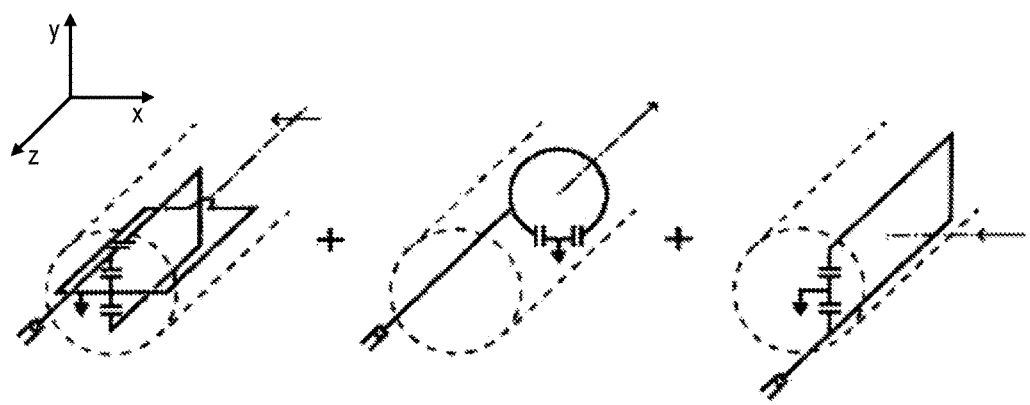
FIGS. 13A-13F show other examples of multiple different coil geometries that can be combined in a single RF coil assembly.
Figures 13D, 13E, 13F:
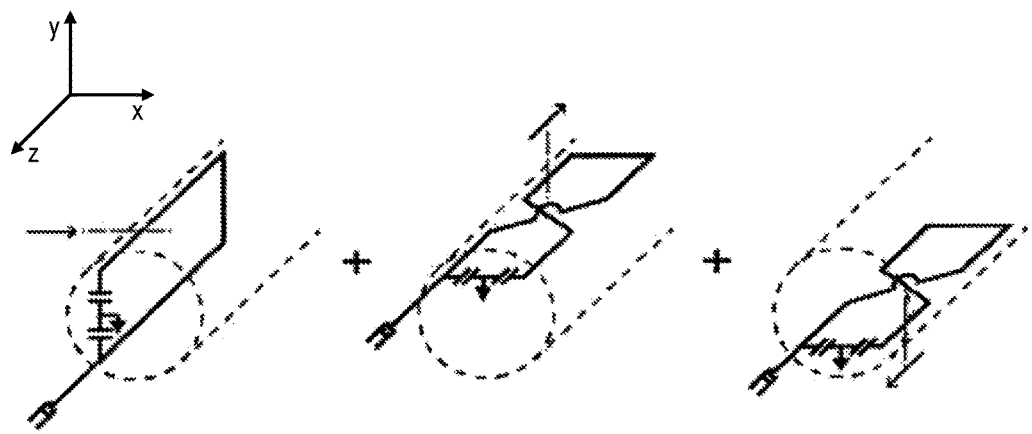

An example in which the three aforementioned coil types are provided together in a geometrically decoupled fashion is shown in FIGS. 12A-12C. The conductor may be a wire, or a planar conductor, among others. This arrangement is particularly attractive given that it generates $B_1$ fields (or is sensitive to a varying magnetic field) in the x-, y-, and z-directions. Therefore, this configuration will provide a high resolution forward looking region of sensitivity regardless of its orientation with respect to the main magnetic field. All of these coils are inherently decoupled by being sensitive to orthogonal magnetic fields. FIGS. 12A-12C show separate views of three orthogonal coils that can be combined within one RF coil assembly 10. FIG. 12A shows a folded butterfly sensitive to fields in the y-direction, FIG. 12B shows a folded stripline coil sensitive to fields in the x-direction, and FIG. 12C shows a loop coil sensitive to fields in the z-direction. All three of these coils may be combined in a single RF coil assembly 10 due to the orthogonality of the fields to which they are individually sensitive.

Another example implementation employs striplines, loops, and butterfly coils that are all arranged to be orthogonal to the $B_0$ field, as shown in FIGS. 13A-13F. To allow for multiple channels orthogonal to the $B_0$ field, a combination of coil geometries are used. Six different coil configurations can be used to image to the left, right, above, below, and forwards of the RF coil assembly 10. To image forwards of the RF coil assembly 10, the coils shown in FIGS. 13A and 13B can be used (folded stripline (FIG. 13A) and loop (FIG. 13B)), to image to the left of the RF coil assembly 10, the coil shown in FIG. 13 C can be used (sideways loop orientation), to image to the right of the RF coil assembly 10, the coil shown in FIG. 13 D can be used (sideways loop orientation), to image above the RF coil assembly 10, the coil in FIG. 13 E can be used (butterfly oriented coplanar with the tissue-facing surface of the absorbent member 14), and to image below the RF coil assembly 10, the coil shown in FIG. 13 F can be used (butterfly oriented coplanar with the tissue-facing surface of the absorbent member 14). All these coils can be combined in a single RF coil assembly 10. For instance, the absorbent member 14 can be composed of multiple different layers, and different coils can be coupled to different layers, as described above.

Although six coils are shown in the FIGS. 13A-13F, it will be understood that there are many such possible arrangements that may be achieved without departing from the scope of the present disclosure. Adding more coils can improve performance. For example, a single RF coil assembly 10 having an elongate absorbent member 14 (e.g., a sponge or the like) could combine two loops to look left and right, two butterflies to look up and down, and a loop and stripline at the tip of the absorbent member 14.

Figure 14:
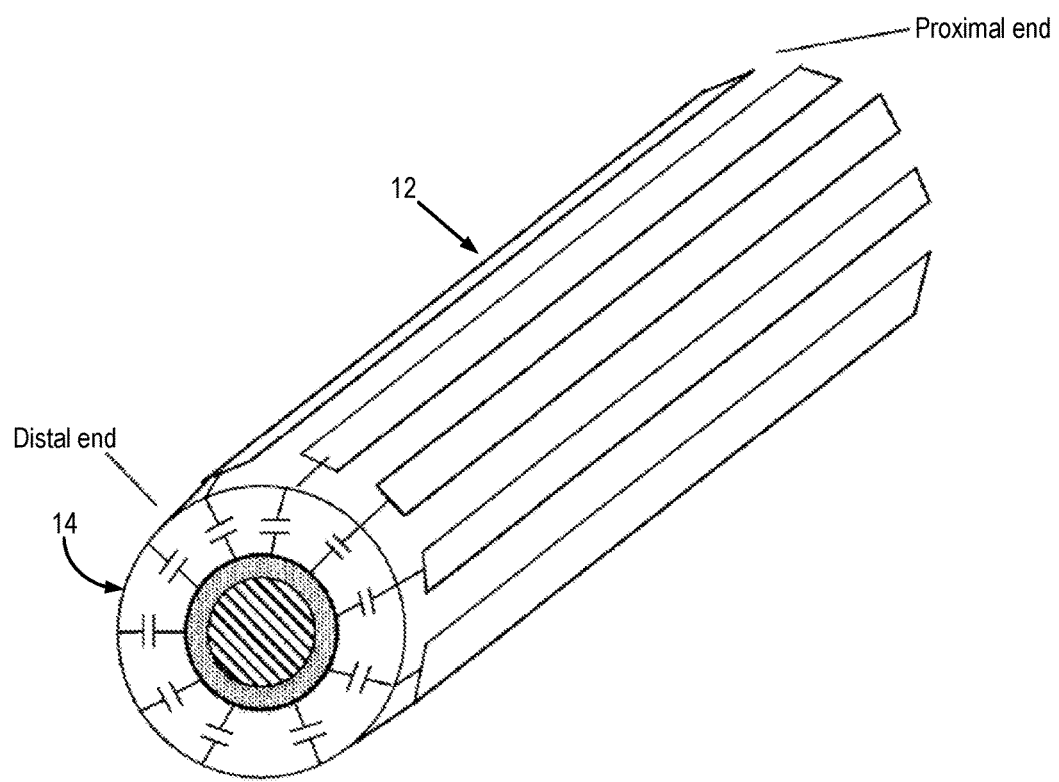
FIG. 14 shows an example of an RF coil assembly that implements an array of stripline coils arranged in parallel about a circumference of a cylindrical absorbent member and extending along a longitudinal axis of the absorbent member.

In FIG. 14, an array of stripline coils are placed parallel to the axis of an elongate absorbent member 14 (e.g., a cylindrical sponge). The stripline coils may be placed equidistant apart around the circumference of the absorbent member 14. Not shown are tuning capacitors from each stripline to a central ground at the proximal end of the absorbent member 14, also not shown are the matching circuit (which could take either forms described above) or preamplifiers, or blocking diodes. Using an array of striplines allows the RF coil 12 to obtain higher SNR in the areas immediately next to the absorbent member 14, though this geometry is more sensitive radially than forward looking.

Figure 15:
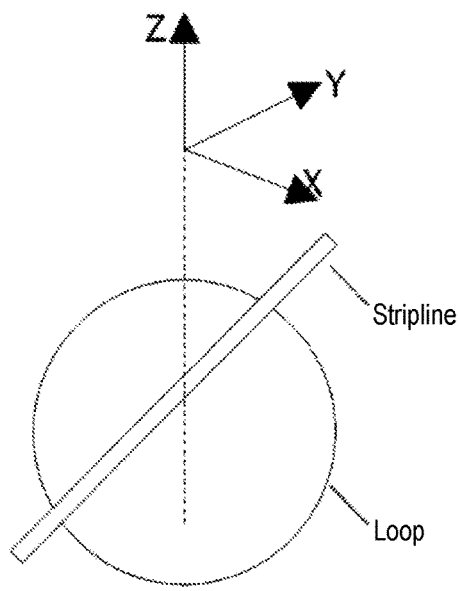
FIG. 15 shows an example of an RF coil assembly that implements a combination of a stripline coil and a loop coil.
Figure 16A:
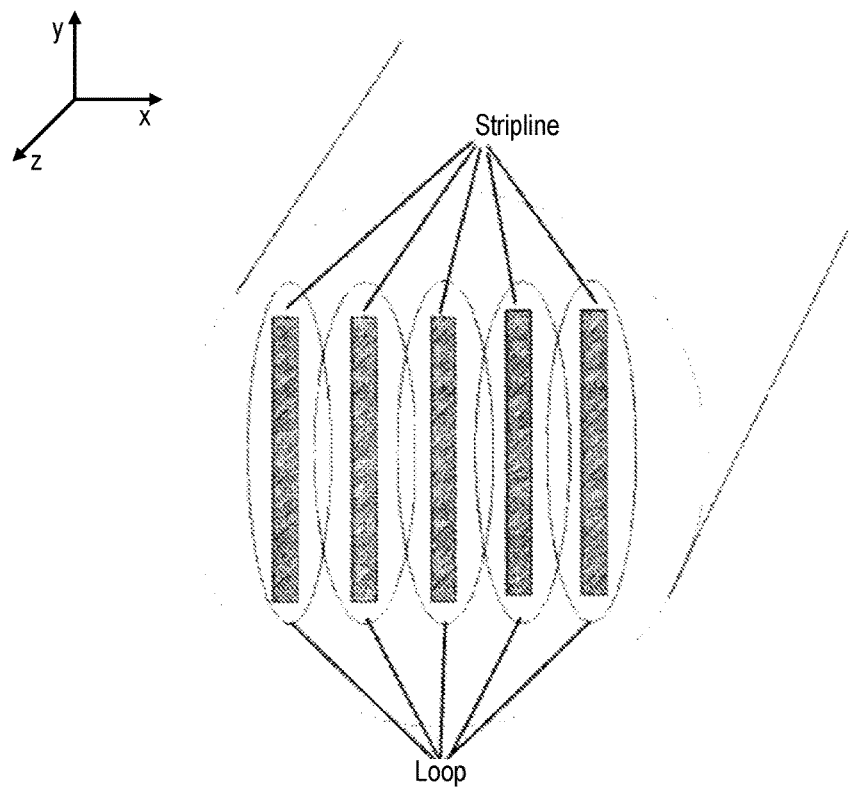
FIG. 16A shows an example of an RF coil assembly that implements an array of stripline coils combined with an array of loop coils.
Figure 16B:
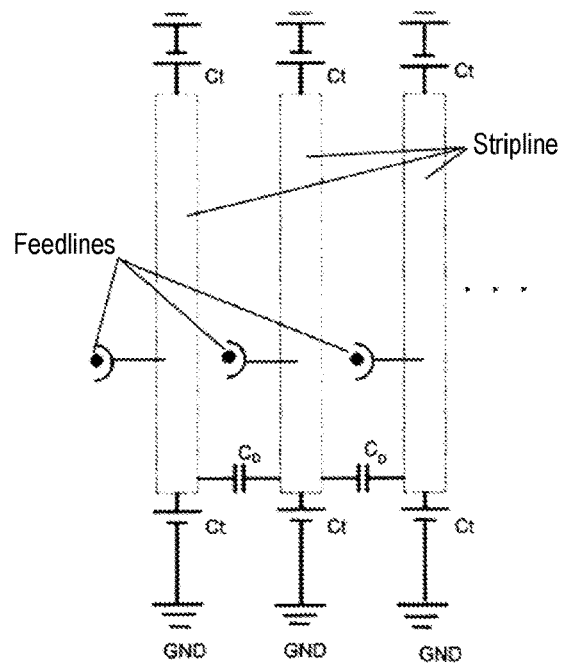
FIG. 16B illustrates an example of the coil configuration of FIG. 16A showing an array circuit that indicates the use of decoupling capacitors (Cd) between elements of a planar stripline array.

Another example embodiment is illustrated in FIGS. 15 and 16 in which striplines in an array are overlaid with loop coil configurations. Stripline coils and loop coils are inherently decoupled. FIG. 15 illustrates a stripline coil and loop coil combination configuration. In this example, the stripline is sensitive to a field in the x-direction while the loop coil is sensitive to a field in the z-direction. Not shown are tuning/matching circuits, preamplifiers, blocking diodes, and so on. The stripline requires a ground circuit (not shown). FIGS. 16A illustrates an alternate embodiment where each stripline coil is overlaid with a loop coil to form an array. Not shown are tuning/matching circuits, preamplifiers, blocking diodes, and so on. Each stripline may have a ground below it, or all striplines may share a common ground. FIG. 16B is a further elaboration of FIG. 16A that illustrates an example of an array circuit that indicates the use of decoupling capacitors (Cd) between elements of a planar stripline array. Each stripline is tuned with two capacitors (Ct) and fed as per FIG. 8C. Each stripline may have a ground, or they may all share a common ground plane (not shown).

Increasing Parallel Imaging through Automatic Coil Detection

In some embodiments, one or more RF coil assemblies 10 may be employed for parallel imaging. Parallel imaging can be accomplished by providing multiple receiving coils, each receiving signals from a slightly different spatial area. Parallel imaging may be performed in either the slice direction, the frequency direction, or the phase encoding direction.

Parallel imaging will be most effective when the body portion of the probe is oriented such that the phase encoding direction of the scanner is perpendicular to the axis of the striplines. However, due to the variances of neurosurgery, the direction of any given RF coil assembly 10 often cannot be known in advance, nor can it be fixed.

To still allow for maximum parallel imaging, a navigation system can be used to track the location of a given RF coil assembly 10 relative to the patient, and the scanner can then choose an oblique slice. Typically, in MRI scanners, the scan planes are chosen in standard orthogonal planes (e.g., axial, sagittal, and coronal). However, it is possible to scan in any plane (referred to as an oblique plane) by choosing the gradients correctly. In order for the scanner to know the direction of a given RF coil assembly 10, the RF coil assembly 10 can be tracked, such as by optical means.

A two-dimensional magnetic resonance image typically has a frequency-encode axis and a phase-encode axis. Parallel imaging can be used (but not exclusively) to speed up the acquisition time along the phase-encode axis by reducing the number of phase-encoding lines that are acquired in a given data acquisition. The frequency-encode axis and the phase-encode axis can correspond to a real axis, such as the x-, y-, or z-axis, or any arbitrary direction. If an array of coils is placed in a scanner such that each coil is arranged on a line that does not correspond to the scanner's definition of the x-, y-, or z-axis, it could be advantageous to define an oblique reference plane so that the axis of the coils does lie along this plane. This will allow maximum time improvement using parallel imaging. The combination of knowledge of the orientation of the RF coil assembly 10 obtained from a tracking system (e.g., an optical tracking system) with the knowledge of the scanner's reference planes will allow a user to vary the scan parameters such that the oblique angles chosen by the scanner maximize the parallel imaging capacity.

Smart Coils

In some embodiments, coil arrays may be employed as smart coils, where the coils are dynamically (e.g., adaptively) controlled, such that only a portion of the coil elements of the array are activated or interrogated during scanning. It will be understood that the present "smart coil" embodiment pertain to any RF coil assembly 10 having an array of coils or to an array of RF coil assemblies 10.

In one example implementation, this may be achieved by an MRI system that is configured to sample signals from the elements of the coil array and to determine when a preselected signal level threshold has been achieved for each coil. When the threshold has been achieved for given coil, that coil is employed (e.g., activated or interrogated) for scanning. This arrangement allows an RF coil assembly 10, or multiple different RF coil assemblies 10, to contain coils that are not necessarily orthogonal to the main magnetic field of the MRI scanner.

As an example, when one or more RF coil assemblies 10 are provided to the patient or subject, a prescan may be conducted with the MRI system. The coils that are sensitive to $B_1$ fields that are perpendicular to the main magnetic field $B_0$ of the MRI scanner will receive a stronger signal than those with a parallel $B_1$ field. These signal values are then employed to determine which coil elements will be activated and which ones will remain off (or, which ones will be employed for obtaining an image, and which will not).

In one example implementation, a criterion for determining which coils to activate or interrogate employs a threshold value, wherein coils receiving signal levels that are below a certain value will remain off (or will not be interrogated) during signal acquisition.

An example of one algorithm that would be employed by a controller, a processor, or the like, in order to determine which coils should be activated or interrogated is described. First, a data signal is received by a given RF coil assembly 10. The data signal (allocated through channels) is then compared to a threshold. The threshold may include a predetermined noise level or known SNR (signal-to-noise ratio). Part of this comparison is to determine whether the signal is above the threshold. If the result is not above the threshold, channels that do not meet this threshold are excluded. If the channels do meet the threshold, then they are combined with the signal to form a merged value or image. An alternate method may include weighing the worse signals (e.g., with a lower weighting value), but still use them to combine in the final image where the weight can be based on the threshold.

In some example methods, the signals from all coils can be sampled again after initially having determined a subset of coils to use. For example, the sampling may occur at a fixed time interval. Alternatively, the sampling may be based on a detected change in the orientation of one or more RF coil assemblies 10 within the $B_0$ field, such as, a changed detected by a tracking system, or a change detected by an inertial sensor associated with the RF coil assembly 10, such as an accelerometer.

In some embodiments, the coils could be selectively activated or interrogated according to a number of criteria. For example, criteria may be based on the signal of one coil compared to some other statistical measure associated with the other coils, such as the average signal magnitude, or criteria based on the a measure of signal to noise ratio, as opposed to signal strength. In another example embodiment, the signals to include could also be based on the orientation of the probe, as detected by a tracking system. The tracking system could be optical, RF, or accelerometer based. There could also be a sensor such as a Hall sensor that is sensitive to the orientation of the static magnetic field.

Example MRI System

Figure 17:
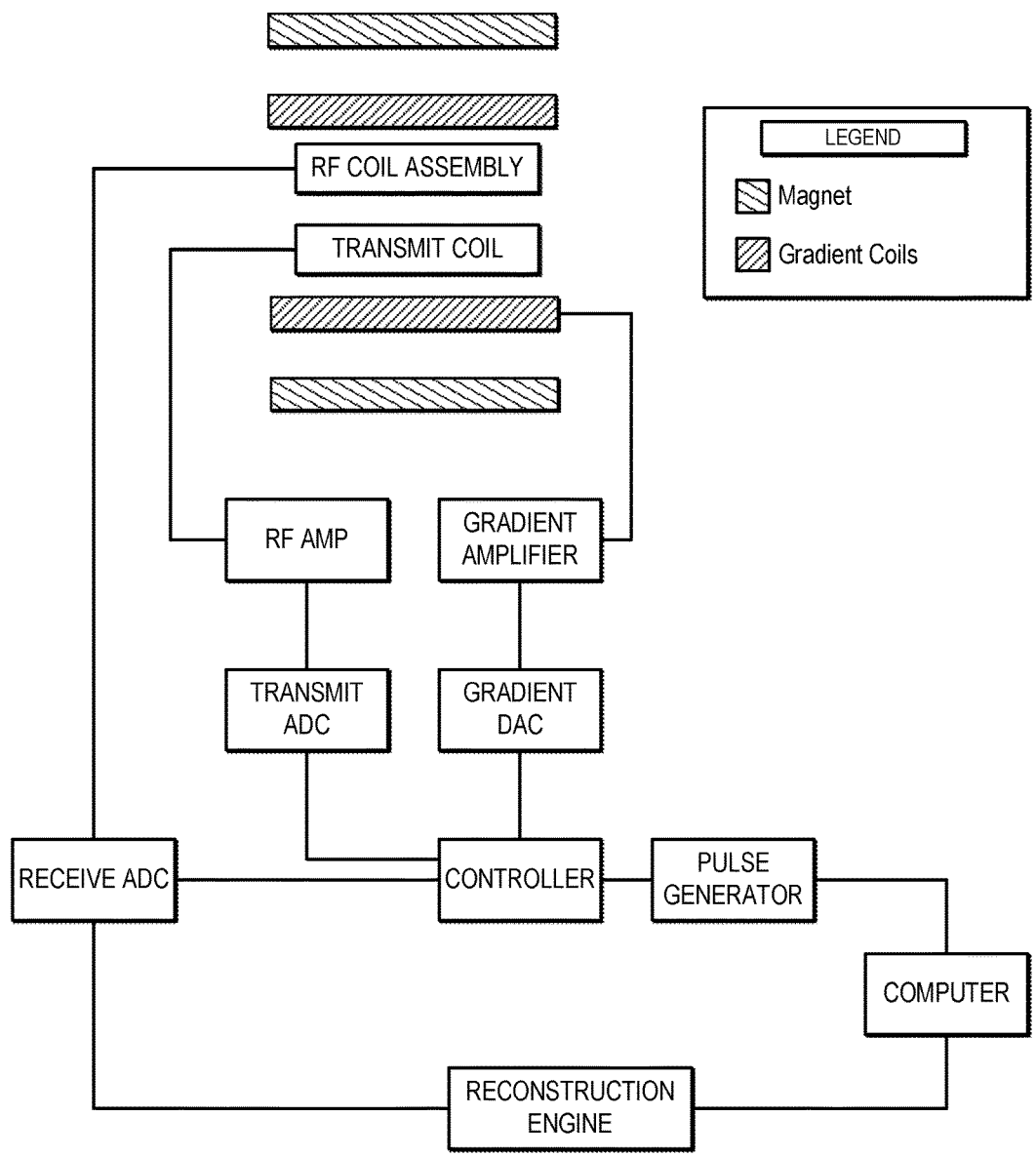
FIG. 17 is a block diagram of one example of an MRI system that can be used in connection with the RF coil assemblies according to the present disclosure.

FIG. 17 provides a schematic illustration of one example of a magnetic resonance imaging ("MRI") system that can be used in connection with the RF coil assemblies described in the present disclosure. The main magnet of an MRI scanner generates a magnetic field ($B_0$) and RF coils are used to generate orthogonal magnetic fields ($B_1$) for exciting the signals during transmission and receiving the magnetic resonance signals during reception. The main magnet could be, for example, a solenoid, single-sided magnet, or a dipole array made with superconducting wire, high temperature superconducting ("HTS") wire, an electromagnet, or a resistive magnet, or a Halbach array of permanent magnets.

The example system can be used with one or more RF coil assemblies according to the present disclosure.

Magnetic resonance imaging can be performed either with separate transmit and receiver coils, or by using the same coil for transmit and receive. The transmit coil may be a head coil, body coil, or a coil or coils associated with one or more RF coil assemblies according to the present disclosure. In some instances, it can be beneficial to use a separate transmit coil to have uniform excitation of tissue. However, by using appropriate pulse sequences, it is possible to still obtain reasonable images from a non-uniform transmit—receive coils.

Other elements included in the example MRI system include a gradient system that includes coils, amplifiers, and DAC converters; an RF system that includes a transmitting and receiving coil, which may or may not be the same device and may or may not be associated with one or more RF coil assemblies according to the present disclosure, in addition to DAC/ADC, and amplifiers. A computer, controller, pulse generator, and reconstruction engine are included.

The controller sends the pulse sequence at the correct time, and the reconstruction engine generates the image from the raw data. The controller and the reconstruction engine, while shown as separate components in FIG. 17, may alternatively be integrated in a single device.

Example MRI System with Rapidly Rampable Field

Figure 18:
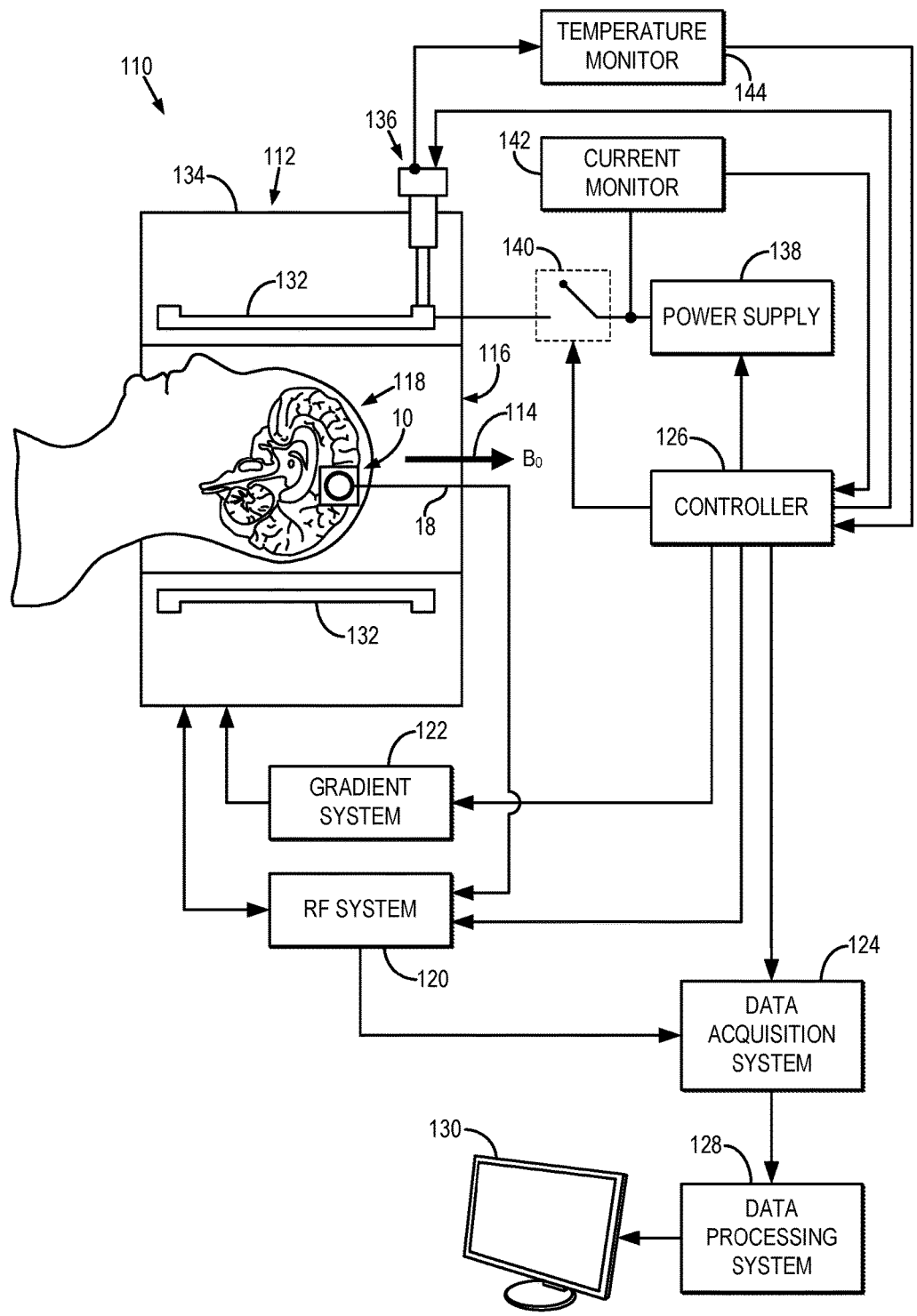
FIG. 18 is a block diagram of another example MRI system that can be used in connection with the RF coil assemblies according to the present disclosure, wherein the magnetic field of the MRI system can be rapidly ramped between two different field strengths.

Another example of an MRI system that can implement the methods described here is shown in FIG. 18. The MRI system 110 can be operated to rapidly ramp its magnetic field from a first magnetic field strength to a second magnetic field strength. Such an MRI system is advantageous for use in an intraoperative setting because the main magnetic field of the scanner can be rapidly ramped up and down as needed during the procedure. The MRI system 110 generally includes a magnet assembly 112 for providing a magnetic field 114 that is substantially uniform within a bore 116 that may hold a subject 118 or other object to be imaged. The magnet assembly 112 supports a radio frequency ("RF") coil that may provide an RF excitation to nuclear spins in the subject 118 or object positioned within the bore 116. The RF coil communicates with an RF system 120 producing the necessary electrical waveforms, as is understood in the art. The RF system 120 may be used as the RF controller 20 for RF coil assemblies 10 according to the present disclosure.

The magnet assembly 112 also supports three axes of gradient coils (not shown) of a type known in the art, and which communicate with a corresponding gradient system 122 providing electrical power to the gradient coils to produce magnetic field gradients, $G_x$, $G_y$, and $G_z$ over time. A data acquisition system 124 connects to RF reception coils, which may include RF coils 12 associated with RF coil assemblies 10 according to the present disclosure, or RF reception coils that are supported within the magnet assembly 112 or positioned within bore 116.

The RF system 120, gradient system 122, and data acquisition system 124 each communicates with a controller 126 that generates pulse sequences that include RF pulses from the RF system 120 and gradient pulses from gradient system 122. The data acquisition system 124 receives magnetic resonance signals from the RF system 120 and provides the magnetic resonance signals to a data processing system 128, which operates to process the magnetic resonance signals and to reconstruct images therefrom. The reconstructed images can be provided to a display 130 for display to a user.

The magnet assembly 112 includes one or more magnet coils 132 housed in a vacuum housing 134, which generally provides a cryostat for the magnet coils 132. The magnet coils are mechanically cooled by a mechanical cryocooler 136, such as a Gifford-McMahon ("GM") cryocooler or a pulse tube cryocooler. In one example configuration, the cryocooler can be a Model RDK-305 Gifford-McMahon cryocooler manufactured by Sumitomo Heavy Industries (Japan). In general, the cryocooler 136 is in thermal contact with the magnet coils 132 and is operable to lower the temperature of the magnet coils 132 and to maintain the magnet coils 132 and a desired operating temperature.

The magnet coils 132 are composed of a superconducting material and therefore provide a superconducting magnet. The superconducting material is preferably selected to be a material with a suitable critical temperature such that the magnet coils 132 are capable of achieving desired magnetic field strengths over a range of suitable temperatures. As one example, the superconducting material can be niobium ("Nb"), which has a transition temperature of about 9.2 K. As another example, the superconducting material can be niobium-titanium ("NbTi"), which has a transition temperature of about 10 K. As still another example, the superconducting material can be triniobium-tin ("$Nb_3Sn$"), which has a transition temperature of about 18.3 K.

The choice of superconducting material will define the range of magnetic field strengths achievable with the magnet assembly 112. Preferably, the superconducting material is chosen such that magnetic field strengths in the range of about 0.0 T to about 3.0 T can be achieved over a range of temperatures that can be suitably achieved by the cryocooler 136. In some configurations, however, the superconducting material can be chosen to provide magnetic field strengths higher than 3.0 T.

The cryocooler 136 is operable to maintain the magnet coils 132 at an operational temperature at which the magnet coils 132 are superconducting, such as a temperature that is below the transition, or critical, temperature for the material of which the magnet coils 132 are composed. As one example, a lower operational temperature limit can be about 4 K and an upper operational temperature limit can be at or near the transition, or critical, temperature of the superconducting material of which the magnet coils 132 are composed.

The current density in the magnet coils 132 in the MRI system 110 is controllable to rapidly ramp up or ramp down the magnetic field 114 generated by the magnet assembly 112 while controlling the temperature of the magnet coils 132 with the cryocooler 136 to keep the temperature below the transition temperature of the superconducting material of which the magnet coils 132 are composed. As one example, the magnetic field 114 can be ramped up or ramped down on the order of minutes, such as fifteen minutes or less.

In general, the current density in the magnet coils 132 can be increased or decreased by connecting the magnet coils 132 to a circuit with a power supply 138 that is in electrical communication with the magnet coils 132 via a switch 140 and operating the power supply 138 to increase or decrease the current in the connected circuit. The switch 140 is generally a superconducting switch that is operable between a first, closed, state and a second, open, state.

When the switch 140 is in its open state, the magnet coils 32 are in a closed circuit, which is sometimes referred to as a "persistent mode." In this configuration, the magnet coils 132 are in a superconducting state so long as the temperature of the magnet coils 132 is maintained at a temperature at or below the transition temperature of the superconducting material of which they are composed.

When the switch 140 is in the closed state, however, the magnet coils 132 and the power supply 138 can be placed in a connected circuit, and the current supplied by the power supply 138 and the current in the magnet coils 132 will try to equalize. For instance, if the power supply 138 is operated to supply more current to the connected circuit, the current in the magnet coils 132 will increase, which will increase the strength of the magnetic field 114. On the other hand, if the power supply 138 is operated to decrease the current in the connected circuit, the current in the magnet coils 132 will decrease, which will decrease the strength of the magnetic field 114.

It will be appreciated by those skilled in the art that any suitable superconducting switch can be used for selectively connecting the magnet coils 132 and power supply 138 into a connected circuit; however, as one non-limiting example, the switch 140 may include a length of superconducting wire that is connected in parallel to the magnet coils 132 and the power supply 138. To operate such a switch 140 into its closed state, a heater in thermal contact with the switch 140 is operated to raise the temperature of the superconducting wire above its transition temperature, which in turn makes the wire highly resistive compared to the inductive impedance of the magnet coils 132. As a result, very little current will flow through the switch 140. The power supply 138 can then be placed into a connected circuit with the magnet coils 132.

When in this connected circuit, the current in the power supply 138 and the magnet coils 132 will try to equalize; thus, by adjusting the current supplied by the power supply 138, the current density in the magnet coils 132 can be increased or decreased to respectively ramp up or ramp down the magnetic field 114. To operate the switch 140 into its open state, the superconducting wire in the switch 140 is cooled below its transition temperature, which places the magnet coils 132 back into a closed circuit, thereby disconnecting the power supply 138 and allowing all of the current to flow through the magnet coils 132.

When the magnet coils 132 are in the connected circuit with the power supply 138, the temperature of the magnet coils 132 will increase as the current in the connected circuit equalizes. Thus, the temperature of the magnet coils 132 should be monitored to ensure that the temperature of the magnet coils 132 remains below the transition temperature for the superconducting material of which they are composed. Because placing the magnet coils 132 into a connected circuit with the power supply 138 will tend to increase the temperature of the magnet coils 132, the rate at which the magnetic field 114 can be ramped up or ramped down will depend in part on the cooling capacity of the cryocooler 136. For instance, a cryocooler with a larger cooling capacity will be able to more rapidly remove heat from the magnet coils 132 while they are in a connected circuit with the power supply 138.

The power supply 138 and the switch 140 operate under control from the controller 126 to provide current to the magnet coils 132 when the power supply 138 is in a connected circuit with the magnet coils 132. A current monitor 142 measures the current flowing to the magnet coils 132 from the power supply 138, and a measure of the current can be provided to the controller 126 to control the ramping up or ramping down of the magnetic field 114. In some configurations, the current monitor 142 is integrated into the power supply 138.

A temperature monitor 144 in thermal contact with the magnet assembly 112 operates to measure a temperature of the magnet coils 132 in real-time. As one example, the temperature monitor 144 can include a thermocouple temperature sensor, a diode temperature sensor (e.g., a silicon diode or a GaAlAs diode), a resistance temperature detector ("RID"), a capacitive temperature sensor, and so on. RTD-based temperature sensors can be composed of ceramic oxynitride, germanium, or ruthenium oxide. The temperature of the magnet coils 132 is monitored and can be provided to the controller 126 to control the ramping up or ramping down of the magnetic field 114.

In operation, the controller 126 is programmed to ramp up or ramp down the magnetic field 114 of the magnet assembly 112 in response to instructions from a user. As mentioned above, the magnetic field 114 can be ramped down by decreasing the current density in the magnet coils 132 by supplying current to the magnet coils 132 from the power supply 138 via the switch 140, which is controlled by the controller 126. Likewise, the strength of the magnetic field 114 can be ramped up by increasing the current density in the magnet coils 132 by supplying current to the magnet coils 132 from the power supply 138 via the switch 140, which is controlled by the controller 126.

The controller 126 is also programmed to monitor various operational parameter values associated with the MRI system 110 before, during, and after ramping the magnetic field 114 up or down. As one example, as mentioned above, the controller 126 can monitor the current supplied to the magnet coils 132 by the power supply 138 via data received from the current monitor 142. As another example, as mentioned above, the controller 126 can monitor the temperature of the magnet coils 132 via data received from the temperature monitor 144. As still another example, the controller 126 can monitor the strength of the magnetic field 114, such as by receiving data from a magnetic field sensor, such as a Hall probe or the like, positioned in or proximate to the bore 116 of the magnet assembly 112.

One or more computer systems can be provided with the MRI system 110 for processing acquired data in accordance with the methods described above. As one example, the data processing system 128 can be used to process the acquired data.

For example, the data processing system 128 can receive magnetic resonance data from the data acquisition system 124 and processes it in accordance with instructions downloaded from an operator workstation. Such processing may include those methods described above for reconstructing images and producing composite images by overlaying image depicting one nuclear spin species with images depicting a different nuclear spin species.

Images reconstructed by the data processing system 128 can be conveyed back to the operator workstation for storage, and real-time images can be stored in a memory, from which they may be output to display 130.

The MRI system 110 may also include one or more networked workstations. By way of example, a networked workstation may include a display; one or more input devices, such as a keyboard and mouse; and a processor. The networked workstation may be located within the same facility as the MRI system 110, or in a different facility, such as a different healthcare institution or clinic.

The networked workstation, whether within the same facility or in a different facility as the MRI system 110, may gain remote access to the data processing system 128 via a communication system. Accordingly, multiple networked workstations may have access to the data processing system 128. In this manner, magnetic resonance data, reconstructed images, or other data may be exchanged between the data processing system 128 and the networked workstations, such that the data or images may be remotely processed by a networked workstation. This data may be exchanged in any suitable format, such as in accordance with the transmission control protocol ("TCP"), the internet protocol ("IP"), or other known or suitable protocols.

The present disclosure has described one or more preferred embodiments, and it should be appreciated that many equivalents, alternatives, variations, and modifications, aside from those expressly stated, are possible and within the scope of the invention.

The invention claimed is:

1. A radio frequency (RF) coil assembly for magnetic resonance imaging in an intraoperative setting, comprising:
   an absorbent member comprising an absorbent material;
   an RF coil coupled to the absorbent member;
   a connecting element comprising a wired connector operatively engaged with the RF coil, wherein the wired connector communicates signals between the RF coil and an RF controller, and maintains a visual indication of a location of the absorbent member relative to tissues adjacent the absorbent member;
   wherein the absorbent member comprises a first layer and a second layer; and
   wherein the first layer is composed of a first absorbent material and the second layer is composed of a second absorbent material, and wherein the RF coil is disposed between the first layer and the second layer.

2. The RF coil assembly as recited in claim 1, wherein the first absorbent material is different from the second absorbent material.

3. The RF coil assembly as recited in claim 1, wherein the first layer is composed of an absorbent material and the second layer is composed of a non-absorbent material.

4. The RF coil assembly as recited in claim 3, wherein the non-absorbent material is a biocompatible material.

5. The RF coil assembly as recited in claim 3, wherein the RF coil is coupled to the second layer.

6. The RF coil assembly as recited in claim 5, wherein the RF coil is disposed on a surface of the second layer that is opposite the first layer.

7. The RF coil assembly as recited in claim 1, wherein the RF coil is coplanar with a tissue-facing surface of the absorbent member.

8. The RF coil assembly as recited in claim 1, wherein the RF coil is one of a loop coil, a stripline coil, or a butterfly coil.

9. The RF coil assembly as recited in claim 1, wherein the RF coil comprises an array of coil elements.

10. The RF coil assembly as recited in claim 9, wherein each coil element in the array of coil elements comprises one of a loop coil, a stripline coil, or a butterfly coil.

11. The RF coil assembly as recited in claim 1, wherein the RF controller comprises an RF receiver and the wired connector communicates magnetic resonance signals received from the RF coil to the RF receiver.

12. The RF coil assembly as recited in claim 1, wherein the RF controller comprises an RF transmitter and the wired connector receives signals from the RF transmitter and communicates the signals to the RF coil to generate a transmit RF field in response thereto.

13. The RF coil assembly as recited in claim 1, wherein the RF controller comprises an RF receiver and an RF transmitter, and wherein the wired connector communicates magnetic resonance signals received from the RF coil to the RF receiver and receives signals from the RF transmitter and communicates the signals to the RF coil to generate a transmit RF field in response thereto.

14. A radio frequency (RF) coil assembly for magnetic resonance imaging in an intraoperative setting, comprising:
   an absorbent member comprising an absorbent material;
   an RF coil coupled to the absorbent member;
   a wireless communications circuit coupled to the absorbent member and in communication with the RF coil, the wireless communications circuit being configured to send signals received by the RF coil to an RF receiver;
   a connecting element comprising a string coupled to the absorbent member to maintain a visual indication of a location of the absorbent member relative to tissues adjacent the absorbent member;
   wherein the absorbent member comprises a first layer and a second layer; and
   wherein the first layer is composed of a first absorbent material and the second layer is composed of a second absorbent material, and wherein the RF coil is disposed between the first layer and the second layer.

15. The RF coil assembly as recited in claim 14, wherein the first absorbent material is different from the second absorbent material.

16. A radio frequency (RF) coil assembly for magnetic resonance imaging in an intraoperative setting comprising;
   an absorbent member comprising an absorbent material;
   an RF coil coupled to the absorbent member;
   a wireless communications circuit coupled to the absorbent member and in communication with the RF coil, the wireless communications circuit being configured to send signals received by the RF coil to an RF receiver;
   a connecting element comprising a string coupled to the absorbent member to maintain a visual indication of a location of the absorbent member relative to tissues adjacent the absorbent member;
   wherein the absorbent member comprising a first layer and a second layer; and wherein the first layer is composed of an absorbent material and the second layer is composed of a non-absorbent material.

* * * * *